(12) United States Patent
Kondou et al.

(10) Patent No.: US 6,254,941 B1
(45) Date of Patent: Jul. 3, 2001

(54) FLUOROALKYLATED LIQUID-CRYSTAL COMPOUNDS, LIQUID-CRYSTAL COMPOSITIONS, AND LIQUID-CRYSTAL DISPLAY ELEMENTS

(75) Inventors: Tomoyuki Kondou; Shuichi Matsui; Kazutoshi Miyazawa; Hiroyuki Takeuchi; Yasuhiro Kubo, all of Ichihara; Fusayuki Takeshita, Kimitsu; Etsuo Nakagawa, Ichihara, all of (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 09/269,286

(22) PCT Filed: Sep. 25, 1997

(86) PCT No.: PCT/JP97/03404
§ 371 Date: Mar. 25, 1999
§ 102(e) Date: Mar. 25, 1999

(87) PCT Pub. No.: WO98/13324
PCT Pub. Date: Apr. 2, 1998

(30) Foreign Application Priority Data

Sep. 25, 1996 (JP) .................................................. 8-272858

(51) Int. Cl.$^7$ ........................... C09K 19/12; C09K 19/52; C07C 25/13; C07C 25/18
(52) U.S. Cl. ................ 428/1.1; 252/299.01; 252/299.66; 570/127; 570/129; 570/132
(58) Field of Search ........................ 252/299.01, 299.66; 428/1.1; 570/127, 129, 132

(56) References Cited

U.S. PATENT DOCUMENTS

| | | | |
|---|---|---|---|
| 5,324,449 | * 6/1994 | Kurmeier et al. | 252/299.01 |
| 5,389,292 | * 2/1995 | Dorsch et al. | 252/299.61 |
| 5,536,442 | * 7/1996 | Reiffenrath et al. | 252/299.01 |

FOREIGN PATENT DOCUMENTS

4301700 * 7/1994 (DE) .

* cited by examiner

Primary Examiner—Shean C. Wu
(74) Attorney, Agent, or Firm—Browdy & Neimark

(57) ABSTRACT

The present invention provides liquid crystalline compounds having a very high voltage holding ratio, very little variation of these properties depending on temperature, high Δn, and good compatibility in the other liquid crystal materials particularly under a low temperature, liquid crystal compositions containing these crystalline compounds, and liquid crystal display devices constituted by using the liquid crystal compositions. The liquid crystalline compounds are represented by general formula (1):

(1)

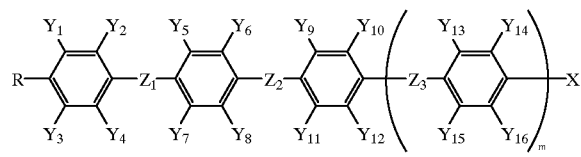

wherein R represents an alkyl, alkoxy or alkoxyalkyl group of 2–20 carbon atoms, and in each group, any 1–3 hydrogen atoms may be replaced by fluorine atoms; X shows an halogen atom or an alkyl group of 1–20 carbon atoms, any methylene groups (—CH$_2$—) not adjacent each other in the alkyl group may be replaced by oxygen atoms, and any one or more hydrogen atoms in the alkyl group may be replaced by fluorine atoms; $Z_1$, $Z_2$ and $Z_3$, each independently, represents —(CH$_2$)$_2$—, —(CH$_2$)$_4$—, —CH$_2$O—, —OCH$_2$—, —(CH$_2$)$_3$O—, —O(CH$_2$)$_3$— or a covalent bond; $Y_1$–$Y_{16}$ each independently represent hydrogen atoms or fluorine atoms, but at least two represent fluorine atoms; m represents 0 or 1, and any atom constituting the compound may be replaced by an isotope thereof.

13 Claims, No Drawings

FLUOROALKYLATED LIQUID-CRYSTAL COMPOUNDS, LIQUID-CRYSTAL COMPOSITIONS, AND LIQUID-CRYSTAL DISPLAY ELEMENTS

This application is a 371 of PCT/JP97/03404 filed Sep. 25, 1997.

TECHNICAL FIELD

The present invention relates to new liquid crystalline compounds and liquid crystal compositions, more particularly, it relates to liquid crystalline compounds having alkyl groups, alkoxy groups and alkoxyalkyl groups, which are substituted by fluorines, liquid crystal compositions containing them, and liquid crystal display devices constituted by using the liquid crystal composition.

BACKGROUND ART

The liquid crystal display devices using the liquid crystalline compound (in this description, the term of a liquid crystalline compound is used as a generic term for a compound exhibiting a liquid crystal phase or a compound not exhibiting a liquid crystal phase but useful as a constituent of a liquid crystal composition) are broadly used in displays of clocks, watches, electronic calculators, word processors and the like.

Lately, much research has been conducted for a TFT type display having properties such as a high contrast and a wide viewing angle. Liquid crystal compositions for TFT need physical properties, such as a high voltage holding ratio, low threshold voltage (Vth), little variation of these properties depending on temperature, broad temperature range of liquid crystal phase and low viscosity. Further, the compositions having a high optical anisotropy (Δn) are useful for improving the response speed.

For these reasons, compounds of fluorine types are preferably used, as described in (1) Japanese Patent Publication 63-13411, (2) Japanese Patent Publication 63-44132, (3) Japanese Patent Laid-open 2-233626, (4) Japanese Patent Laid-open 2-501311, (5) Japanese Patent Laid-open 3-500413 and (6) DE4301700, many synthesis methods and researches have been done.

DISCLOSURE OF INVENTION

The present invention aims to provide liquid crystalline compounds having 1) a very high voltage holding ratio, 2) very little variation of these properties depending on temperature, 3) high Δn, and 4) good compatibility with other liquid crystal materials particularly under a low temperature, liquid crystal compositions containing these crystalline compounds, and liquid crystal display devices constituted by using the liquid crystal compositions.

The present inventors have earnestly studied to resolve the above problems and have completed the studies by obtaining the liquid crystalline compounds having the above properties. The compounds are represented by general formula (1);

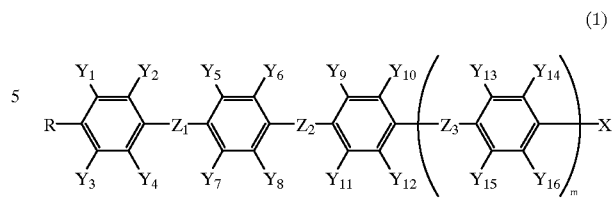

wherein R represents an alkyl, alkoxy or alkoxyalkyl group of 2–20 carbon atoms, and in each group, any 1–3 hydrogen atoms may be replaced by fluorine atoms; X shows a halogen atom or an alkyl group of 1–20 carbon atoms, any methylene groups ($-CH_2-$) not adjacent each other in the alkyl group may be replaced by oxygen atoms, and any one or more hydrogen atoms in the alkyl group may be replaced by fluorine atoms; $Z_1$, $Z_2$ and $Z_3$, each independently, represents $-(CH_2)_2-$, $-(CH_2)_4-$, $-CH_2O-$, $-OCH_2-$, $-(CH_2)_3O-$, $-O(CH_2)_3-$ or a covalent bond; $Y_1-Y_{16}$ each independently represent hydrogen atoms or fluorine atoms, but at least two represent fluorine atoms; m represents 0 or 1, and any atom constituting the compound may be replaced by an isotope thereof.

A part of the compounds represented by general formula (1) are formally included in the compounds having general formula described in the above references (5) and (6). However, in these references, there is no description of data such as values of physical properties of the compounds of the present invention, and definite or embodied characteristics of these compounds, so that the present invention is not suggested.

The compounds represented by general formula (1) can be classified as follows.

In the following, R, X and $Z_1-Z_3$ have the same meaning as described above, P represents a 1,4-phenylene group in which any one or more hydrogen atoms may be replaced by fluorine atoms.

Compounds having 3 six-membered rings:

| | |
|---|---|
| R-P-P-P-X | (1a) |
| R-P-$Z_1$-P-P-X | (1b) |
| R-P-P-$Z_2$-P-X | (1c) |
| R-P-$Z_1$-P-$Z_2$-P-X | (1d) |

Compounds having 4 six-membered rings:

| | |
|---|---|
| R-P-P-P-P-X | (1e) |
| R-P-$Z_1$-P-P-P-X | (1f) |
| R-P-P-$Z_2$-P-P-X | (1g) |
| R-P-P-P-$Z_3$-P-X | (1h) |
| R-P-$Z_1$-P-$Z_2$-P-P-X | (1i) |
| R-P-$Z_1$-P-P-$Z_3$-P-X | (1j) |
| R-P-P-$Z_2$-P-$Z_3$-P-X | (1k) |
| R-P-$Z_1$-P-$Z_2$-P-$Z_3$-P-X | (1l) |

In these compounds, particularly, the compounds represented by formulae (1a)–(1c) and formulae (1e)–(1h) are preferably used for attaining the objects of the present invention.

In these formulas, R is an alkyl, alkoxy or alkoxyalkyl group of 2–20 carbon atoms, and in each group, any 1–3 hydrogen atoms may be replaced by fluorine atoms. And specifically, fluoroalkyl groups of straight chain such as 1-fluoroethyl, 2-fluoroethyl, 1-fluoropropyl, 2-fluoropropyl, 3-fluoropropyl, 1-fluorobutyl, 2-fluorobutyl, 3-fluorobutyl, 4-fluorobutyl, 1-fluoropentyl, 2-fluoropentyl, 3-fluoropentyl, 4-fluoropentyl, 5-fluoropentyl, 6-fluorohexyl, 7-fluoroheptyl, 10-fluorodecyl, 15-fluoropentadecyl, 20-fluoroicosyl, 1,1-difluoroethyl, 1,2-difluoroethyl, 2,2-difluoroethyl, 1,1-difluoropropyl, 2,2-difluoropropyl, 3,3-difluoropropyl, 1,2-difluoropropyl, 1,3-difluoropropyl, 2,3-difluoropropyl, 3,3-difluoropentyl, 5,5-difluoropentyl, 15,15-difluoropentadecyl, 1,1,2-trifluoroethyl, 1,2,2-trifluoroethyl, 2,2,2-trifluoroethyl, 1,1,2-trifluoropropyl, 1,1,3-trifluoropropyl, 1,2,2-trifluoropropyl, 1,3,3-trifluoropropyl, 2,2,3-trifluoropropyl, 1,2,3-trifluoropropyl, 3,3,5-trifluoropentyl and 16,17,17-trifluoroheptadecyl; and fluoroalkyl groups of branched chains such as 1-methyl-2-fluoroethyl, 2-ethyl-3-fluoropropyl, 2-methyl-4-fluorobutyl, 2,4-dimethyl-5-fluoropentyl, 3-ethyl-5-fluorohexyl and 5-trifluoromethyldecyl can be exemplified.

As the fluoroalkoxy groups, 1-fluoroethoxy, 2-fluoroethoxy, 1-fluoropropoxy, 2-fluoropropoxy, 3-fluoropropoxy, 1-fluorobutoxy, 2-fluorobutoxy, 3-fluorobutoxy, 4-fluorobutoxy, 1-fluoropentyloxy, 2-fluoropentyloxy, 3-fluoropentyloxy, 4-fluoropentyloxy, 5-fluoropentyloxy, 13-fluorotridecyloxy, 1,1-difluoroethoxy, 2,2-difluoroethoxy, 1,2-difluoroethoxy, 1,1-difluoropropoxy, 2,2-difluoropropoxy, 3,3-difluoropropoxy, 1,2-difluoropropoxy, 1,3-difluoropropoxy, 1,1-difluorobutoxy, 2,2-difluorobutoxy, 3,3-difluorobutoxy, 4,4-difluorobutoxy, 1,2-difluorobutoxy, 1,3-difluorobutoxy, 1,4-difluorobutoxy, 2,3-difluorobutoxy, 2,4-difluorobutoxy, 3,4-difluorobutoxy, 1,1-difluoropentyloxy, 2,2-difluoropentyloxy, 3,3-difluoropentyloxy, 4,4-difluoropentyloxy, 5,5-difluoropentyloxy, 1,2-difluoropentyloxy, 1,3-difluoropentyloxy, 1,4-difluoropentyloxy, 1,5-difluoropentyloxy, 2,3-difluoropentyloxy, 2,4-difluoropentyloxy, 2,5-difluoropentyloxy, 3,4-difluoropentyloxy, 3,5-difluoropentyloxy, 4,5-difluoropentyloxy, 16,16-difluorohexadecyloxy, 1,1,2-trifluoroethoxy, 2,2,2-trifluoroethoxy, 1,1,2-trifluoropropoxy, 1,1,3-trifluoropropoxy, 1,2,2-trifluoropropoxy, 1,3,3-trifluoropropoxy, 2,2,3-trifluoropropxy, 1,2,3-trifluoropropxy, 3,3,3-trifluoropropxy, 2,4,4-trifluorobutoxy, 3,4,4-trifluorobutoxy, 4,4,4-trifluorobutoxy and 11,11,11-trifluoroundecyloxy can be exemplified.

As the alkoxy alkyl groups replaced by fluorines, fluoromethoxy methyl, 1-fluoro-1-methoxymethyl, (1-fluoroethoxy)methyl, (2-fluoro ethoxy)methyl, 1-fluoro-1-ethoxymethyl, (1-fluoropropoxy)methyl, (2-fluoropropoxy) methyl, (3-fluoropropoxy)methyl, 1-fluoro-1-propoxymethyl, (1-fluorobutoxy) methyl, (2-fluorobutoxy)methyl, (3-fluorobutoxy)methyl, (4-fluorobutoxy) methyl, 1-fluoro-1-butoxymethyl, 1-(fluoromethoxy)ethyl, 2-(fluoromethoxy) ethyl, 1-fluoro-2-methoxyethyl, 2-(1-fluoroethoxy)ethyl, 2-(2-fluoroethoxy)ethyl, 2-(1-fluoropropoxy)ethyl, 2-(2-fluoropropoxy) ethyl, 2-(3-fluoropropoxy)ethyl, 2-(fluoromethoxy)propyl, 3-(fluoro-methoxy)propyl, 2-(1-fluoroethoxy) propyl, 3-(1-fluoroethoxy)propyl, 3-(2-fluoroethoxy)propyl, 3-(3-fluoroethoxy)propyl, (difluoromethoxy) methyl, 1-fluoro-1-(fluoromethoxy)methyl, (1,1-difluoroethoxy)methyl, (1,2-difluoroethoxy)methyl, (2,2-difluoroethoxy)methyl, (1,1-difluoropropoxy)methyl, (2,2-difluoropropoxy)methyl, (3,3-difluoro propoxy)methyl, (1,2-difluoropropoxy)methyl, (1,3-difluoropropoxy)methyl, (2,3-difluoro-propoxy)methyl, 2-(difluoromethoxy)ethyl, 2-(1,1-difluoroethoxy)ethyl, 2-(2,2-difluoroethoxy)ethyl, 2-(1,2-difluoroethoxy)ethyl, 2-(1,1-difluoropropoxy)ethyl, 2-(2,2-difluoropropoxy)ethyl, 2-(3,3-difluoro-propoxy) ethyl, 2-(1,2-difluoropropoxy)ethyl, 2-(1,3-difluoropropoxy)ethyl, 2-(2,3-difluoropropoxy)ethyl, 2-(4,4-difluorobutoxy)ethyl, 3-(difluoro-methoxy)propyl, 3-(2,2-difluoroethoxy)propyl, 3-(1,2-difluoroethoxy) propyl, 3-(2,2-difluoropropoxy) propyl, 3-(3,3-difluoropropoxy)propyl, 4-(difluoromethoxy)butyl, 4-(4,4-difluorobutoxy)butyl, 5-(difluoromethoxy)pentyl, (trifluoromethoxy)methyl, (1,1,2-trifluoroethoxy)methyl, (1,2,2-trifluoroethoxy)methyl, (2,2,2-trifluoroethoxy)methyl, (2,2,3-trifluoropropoxy) methyl, (3,3,3-trifluoropropoxy)methyl, (4,4,4-trifluorobutoxy)methyl, (5,5,5-trifluoropentyloxy)methyl, 2-(trifluoro-methoxy)ethyl, (2,2,2-trifluoroethoxy)ethyl, (3,3,3-trifluoropropoxy)-ethyl, (4,4,4-trifluorobutoxy)ethyl, (5,5,5-trifluoropentyloxy)ethyl, (2,2,2-trifluoroethoxy) propyl, 3-(trifluoromethoxy)propyl, (3,3,3-trifluoropropoxy)propyl, (4,4,4-trifluorobutoxy)propyl, (5,5,5-trifluoropentyloxy)propyl, 4-(trifluoromethoxy)butyl, (2,2,2-trifluoro-oethoxy)butyl, (3,3,3-trifluoropropoxy) butyl, (4,4,4-trifluorobutoxy) butyl, (5,5,5-trifluoropentyloxy)butyl, 5-(trifluoromethoxy)pentyl, (2,2,2-trifluoroethoxy)pentyl, (3,3,3-trifluoropropoxy)pentyl, (4,4,4-trifluorobutoxy)pentyl, (5,5,5-trifluoropentyloxy) pentyl can be exemplified. Moreover, in the above R, the groups having the branched chains may be optically active groups, and when R is the optically active group, the compound is useful as a chiral dopant.

The number of fluorine atoms in R of the group is selected from any number of 1–3, preferably 1 or 2, because as the number of the fluorine atoms increases, the viscosity increases to some degree, and $\Delta\epsilon$ etends to decrease.

X is a halogen atom or an alkyl group of 1–20 carbon atoms, concretely, it is Br, Cl, F, I, —$CF_3$, —$CF_2H$, —$CFH_2$, —$OCF_3$, —$OCF_2H$, and the same monovalent group as the above R.

In general formula (1), $Z_1$, $Z_2$ and $Z_3$, each independently, represents —$(CH_2)_2$—, —$(CH_2)_4$—, —$CH_2O$—, —$OCH_2$—, —$(CH_2)_3O$—, —$O(CH_2)_3$— or a covalent bond, preferably, it represents —$(CH_2)_2$—, —$CH_2O$—, —$OCH_2$— or a covalent bond.

The compounds wherein m is 0 show a liquid crystal phase (or a melting point) at a relatively middle temperature, and the compounds wherein m is 1 show a high transition temperature of an isotropic phase (or a melting point).

When X is a strong electrophilic group such as a halogen atom, $CF_3$ or the like, it shows very high positive $\Delta\epsilon$ and very low threshold voltage.

$Y_1$–$Y_{16}$ are each independently selected from hydrogen atoms or fluorine atoms. As the number of the fluorine atoms increases, the viscosity tends to increase, and $\Delta\epsilon$ can be higher and then the compatibility is improved.

The compound having an atom replaced by an isotope in the molecular is also preferable because it shows similar physical properties.

By suitably selecting these substituted groups and bond groups, compounds having desired physical properties can be obtained.

Although the liquid crystalline compounds of the present invention represented by general formula (1)may be prepared by a method of common organic synthesis, as an example, the compounds may be easily prepared by the following method.

(scheme 1)
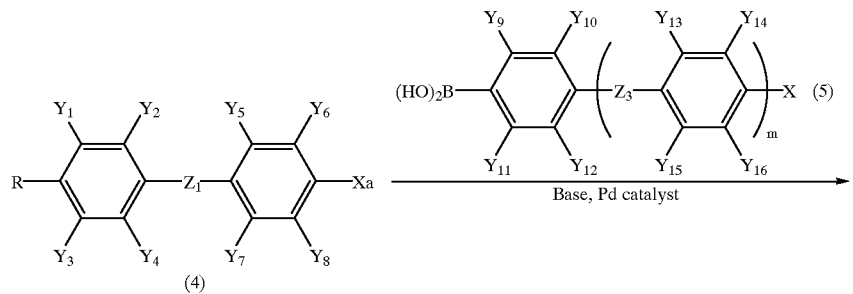
(scheme 2)
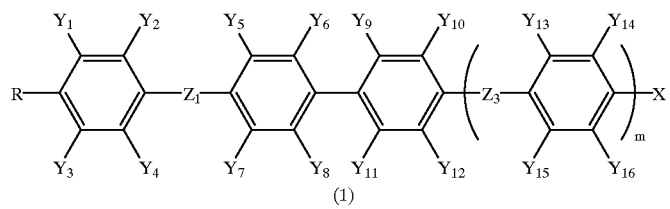
(scheme 3)
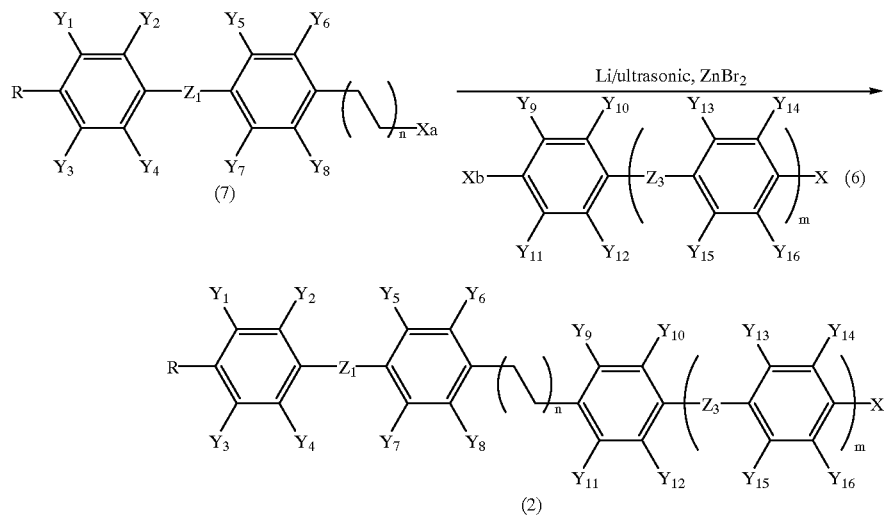

-continued (scheme 4)

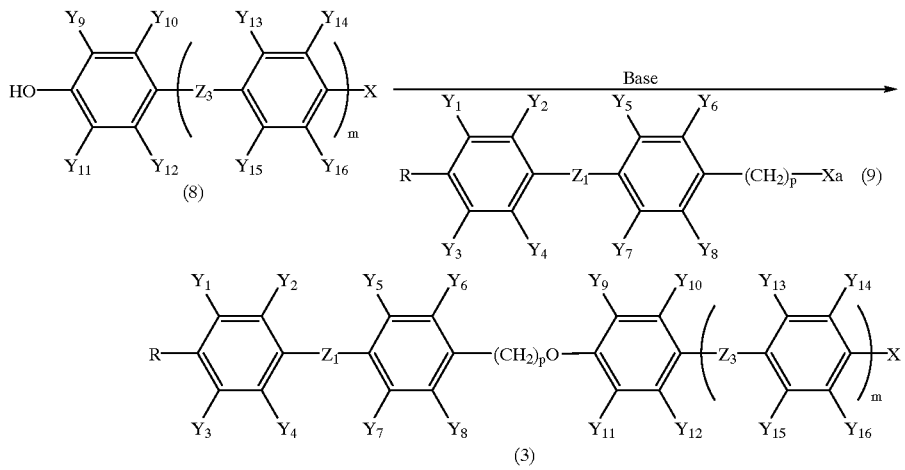

wherein R, X, $Y_1$–$Y_{16}$, $Z_1$, $Z_3$ and m have the same meaning as described above, Xa and Xb are halogen atoms (particularly, bromine or iodine), n is 1 or 2, and p is 1 or 3.

Namely, as shown in scheme 1, in mixed solvent of three ingredients; toluene or xylene, alcohol such as ethanol, and water; compound (4) and compound (5) can be reacted in the presence of a base such as $K_2CO_3$ or $Na_2CO_3$ and a catalyst such as carbon-carried palladium (Pd—C), $Pd(PPh_3)_4$ or $PdCl_2(PPh_3)_2$ to produce an embodied compound (1) of the present invention. Further, as shown in scheme 2, after reacting compound (4) with a lithium compound such as n-BuLi or sec-BuLi and a zinc compound such as $ZnCl_2$ or $ZnBr_2$, the reactant may be reacted with compound (6) to obtain the above compound (1).

As shown in scheme 3, after reacting compound (7) with Li, by reacting the compound with a zinc compound and compound (6), example compound (2) of the present invention can be prepred.

As shown in scheme 4, in the presence of a base such as sodium amide (J. B. Right et al., Journal of the American chemical Society, 70, 3098 (1948)), potassium carbonate (W. T. Olson et al., Journal of the American Chemical Society, 69, 2451(1947)), triethylamine (R. L. Merker et al., The Journal of Organic Chemistry, 26, 5180 (1961)), sodium hydroxide (C. Wilkins, Synthesis, 1973, 156), potassium hydroxide (J. Rebek et al., The Journal of Organic Chemistry, 44, 1485 (1979)), barium hydroxide (Kawabe et al., The Journal of Organic Chemistry, 37, 4210 (1972)) or sodium hydride (C. J. Stark, Tetrahedron Letters, 22, 2089 (1981), K. Takai et al., Tetrahedron Letters, 21, 1657 (1980)), in a solvent such as dimethylsulfoxide, dimethylformamide, 1,2-dimethoxyethane, tetrahydrofuran, hexamethylphosphoric triamide or toluene, compound (8) can be reacted with compound (9) to obtain compound example (3) of the present invention.

As a method for introducing afluorine into group R, for example, the following method can be indicated.

(scheme 5)

-continued (scheme 6)

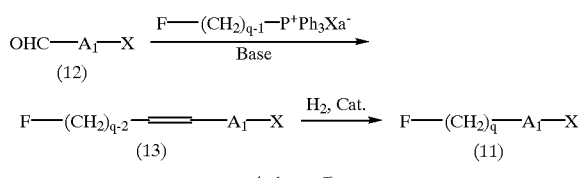

(scheme 7)

(scheme 8)

(scheme 9)

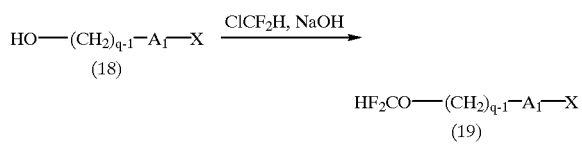

(scheme 10)

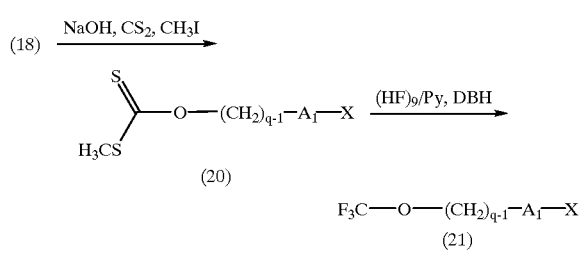

wherein X and Xa have the same meaning as described above, q shows an integer of 2–20. In the above schemes 5–10, $A_1$ can be one of the following groups.

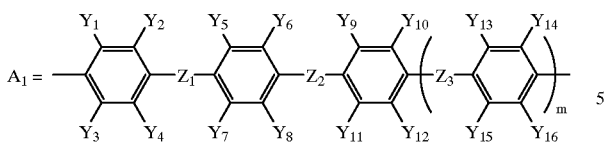

wherein $Y_1$–$Y_{16}$, $Z_1$–$Z_3$ and m have the same meaning as described above.

Namely, as shown in scheme 5, by using fluorinating agent such as diethylaminosulfur trifluoride (DAST) (W. J. Middleton et al., The Journal of Organic Chemistry, 40, 574 (1975), S. Rozen et al., Tetrahedron Letters, 41, 111 (1985), M. Hudlicky, Organic Reactions, 35, 513 (1988), P. A. Messina et al., Journal of Fluorine Chemistry, 42, 137 (1989)), morpholinosulfur trifluoride (K. C. Mange et al., The Journal of Fluorine Chemistry, 43, 405 (1989)) or hexafluoropropene-diethylamine reagent (Ishikawa et al., Bulletin of the Chemical Society of Japan, 52, (11), 3377 (1979)), compound (10) can be fluorinated to obtain compound (11). Further, as shown in scheme 6, after conducting a Wittig reaction of compound (12) with a phosphonium salt, in the presence of a catalyst such as Raney nickel or Pd—C, the compound can be reduced with hydrogen to obtain compound (11).

As shown in scheme 7, compound (14) can be fluorinated with DAST to prepare compound (15).

As shown in scheme 8, compound (16) can be reacted with sodium trifluoroacetate/copper iodide (I) (G. E. Carr et al., Journal of the chemical Society Perkin Trans Actions I, 921 (1988) or methyl fluorosulphonyl difluoroacetate/copper iodide (I) (Q. Y. Chen et al., Journal of the Chemical Society Chemical Communications, 705 (1989)) to obtain compound (17).

As shown in scheme 9, compound (18) can be reacted with chlorodifluoromethane/sodium hydroxide (Japanese Patent Laid-open No. 3-500413) to obtain compound (19). Otherwise, by a method of Chen et al. (The Journal of Fluorine Chemistry, 44, 433 (1989)), compound (19) may be obtained.

As shown in scheme 10, compound (18) can be reacted by a method of Albert et al. (Synthetic Communications, 19, 547(1989)) to obtain xanthate (20) and then fluorinated by a method of Kurohoshi et al. (Tetrahedron Letters, 33, 29, 4173 (1992)) to obtain compound (21).

A substituted group of X can be easily obtained by using a raw material having in advance the substituted group, or by introducing at an optional step by the same method as in schemes 5–10.

The raw material, a halogen compound and a dihydroxyborane derivative can be also produced by a common organic synthetic method, for example, these can be easily prepared by the following method.

(scheme 11)

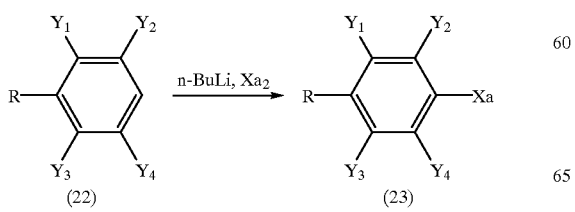

-continued
(scheme 12)

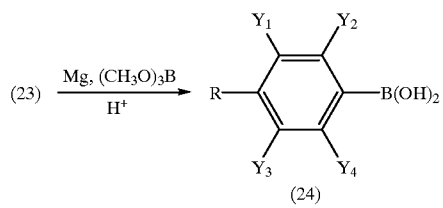

wherein R, $Y_1$–$Y_4$ and Xa have the same meaning as described above.

Namely, as shown in scheme 11, by reaction of compound (22) with a lithium compound such as n-BuLi and iodine or bromine, halogen compound (23) can be prepared.

As shown in scheme 12, after reacting compound (23), a Grignard reagent, which is prepared from magnesium, and a borane derivative such as trimethoxyborane or triisopropyloxyborane, the reactant can be hydrolyzed with hydrochloric acid and the like to obtain dihydroxyborane derivative (24).

By combining the reactions described above taking the properties of the compounds into consideration, the compounds of the present invention can be prepared.

These exemplified reactions are known, and if necessary, the other known reactions can be properly used.

The liquid crystalline compounds thus obtained have a very high voltage holding ratio, very little variation of these properties depending on temperature and high Δn. These compounds can be easily mixed with several liquid crystal materials, and have good compatibility with the other liquid crystalline compounds under low temperature.

Moreover, these liquid crystalline compounds of the present invention have physically and chemically enough stability under general conditions using the liquid crystal display devices, and these are very excellent as a constituent of a nematic liquid crystal composition.

The compounds of the present invention can be preferably used as a constituent of liquid crystal compositions for a display mode such as TN, STN, TFT or the like.

In the following, the liquid crystal compositions of the present invention are described. The liquid crystal compositions of the present invention preferably contain at least one compound represented by general formula (1) at 0.1–99.9 % by weight so as to develop good properties.

More particularly, the liquid crystal composition provided by the present invention is obtained by mixing the first component containing at least one compound of general formula (1) and the compounds suitably selected from the group of compounds represented by general formula (2)–(9) at an appropriate ratio.

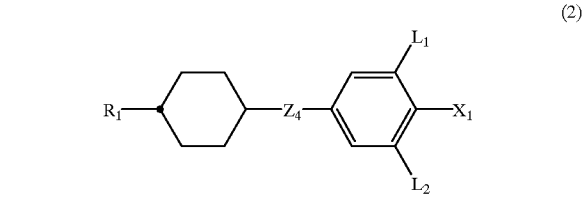

-continued

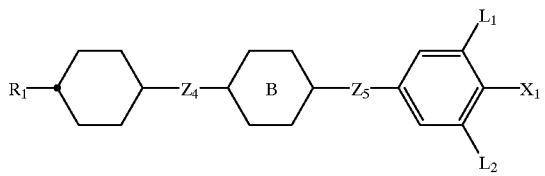
(3)

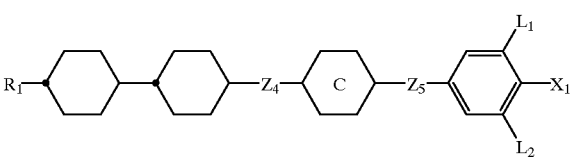
(4)

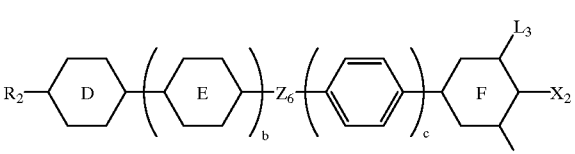
(5)

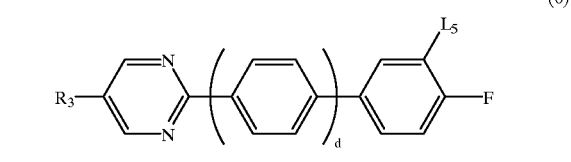
(6)

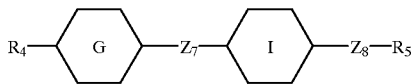
(7)

(8)

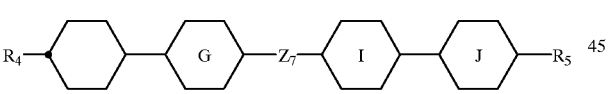
(9)

wherein $R_1$ represents an alkyl group of 1–10 carbon atoms, any nonadjacent methylene groups in the said alkyl group may be substituted by oxygen atoms or —CH=CH—, and any hydrogen atoms in the alkyl group may be substituted by fluorine atoms; $X_1$ represents a fluorine atom, a chlorine atom, —OCF$_3$, —OCF$_2$H:, —CF$_3$, —CF$_2$H, —CFH$_2$, —OCF$_2$CF$_2$H or —OCF$_2$CFHCF$_3$; $L_1$ and $L_2$ independently represent a hydrogen atom or a fluorine atom; $Z_4$ and $Z_5$ independently represent a 1,2-ethylene group, 1,4-butylene group, —COO—, —CF$_2$O—, —OCF$_2$—, —CH=CH— or a covalent bond, ring B represents trans-1,4-cyclohexylene, 1,3-dioxane-2,5-diyl or 1,4-phenylene whose hydrogen atoms may be substituted by fluorine atoms; ring C represents trans-1,4-cyclohexylene, or 1,4-phenylene whose hydrogen atoms may be substituted by fluorine atoms.

$R_2$ and $R_3$ independently represent an alkyl group of 1–10 carbon atoms, any nonadjacent methylene groups in the alkyl group may be substituted by oxygen atoms or —CH=CH—, and any hydrogen atoms in the alkyl group may be substituted by fluorine atoms, $X_2$ represents —CN group or —C≡C—CN group; ring D represents trans-1,4-cyclohexylene, 1,4-phenylene, 1,3-dioxane-2,5-diyl or pyrimidine-2,5-diyl; ring E represents trans-1,4-cyclohexylene, 1,4-phenylene whose hydrogen atoms may be substituted by fluorine atoms, or pyrimidine-2,5-diyl; ring F represents trans-1,4-cyclohexylene or 1,4-phenylene; $Z_6$ represents a 1,2-ethylene group, —COO— or a covalent bond; $L_3$, $L_4$ and $L_5$ independently represent a hydrogen atom or a fluorine atom; b, c and d independently represent 0 or 1;

$R_4$ and $R_5$ independently represent an alkyl group of carbon atoms of 1–10, any nonadjacent methylene groups in the alkyl group may be substituted by oxygen atoms or —CH=CH—, and any hydrogen atoms in the alkyl group may be substituted by fluorine atoms; ring G, ring I and ring J independently represent trans-1,4-cyclohexylene, pyrimidine2,5-diyl, or 1,4-phenylene whose hydrogen atoms may be substituted by fluorine atoms; $Z_7$ and $Z_8$ independently represent —C≡C—, —COO—, —CH$_2$CH$_2$—, —CH=CH— or a covalent bond; and any atom constituting these compounds may be subsituted by its isotope.

The following compounds can be preferably exemplified as the compounds of general formula (2)–(4), which are used in the present invention.

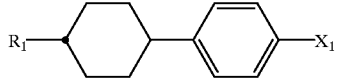
(2-1)

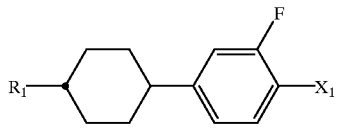
(2-2)

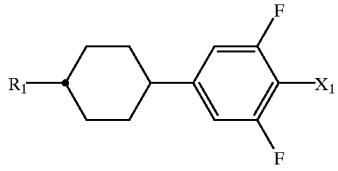
(2-3)

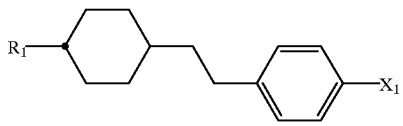
(2-4)

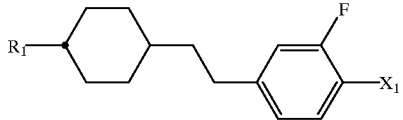
(2-5)

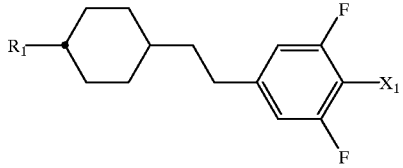
(2-6)

(2-7) 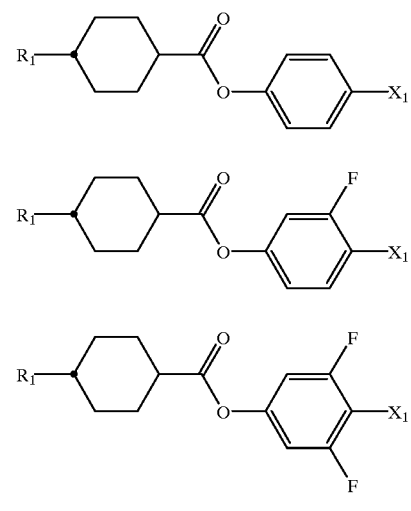
(2-8)
(2-9)
(3-1) 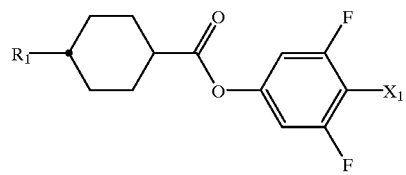
(3-2)
(3-3) 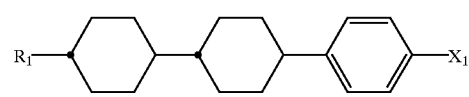
(3-4)
(3-5)
(3-6) 
(3-7)
(3-8) 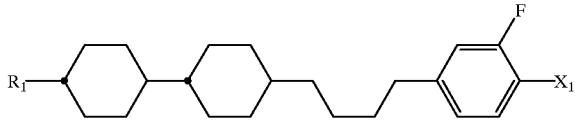
(3-9) 
(3-10) 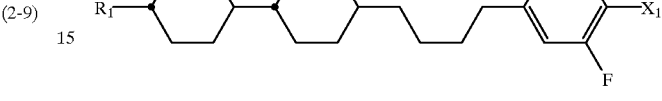
(3-11) 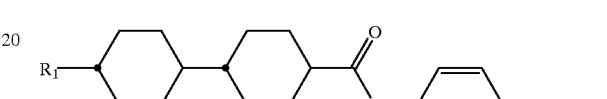
(3-12) 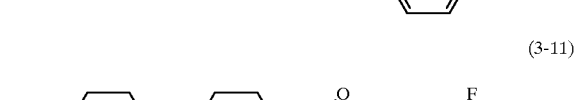
(3-13) 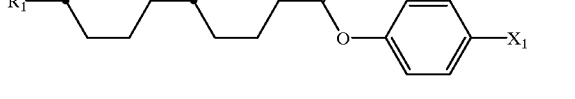
(3-14) 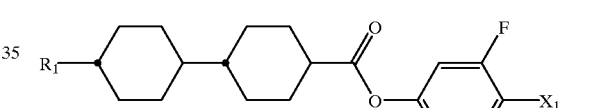
(3-15) 

(3-16)
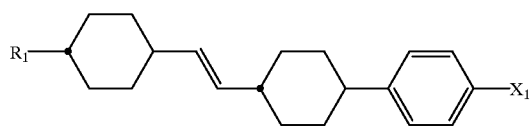
(3-17)
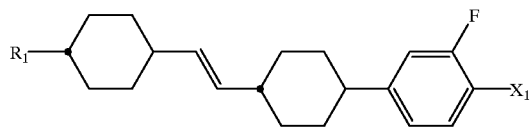
(3-18)
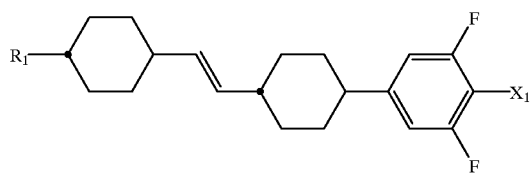
(3-19)
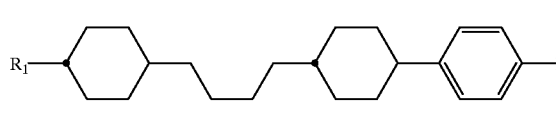
(3-20)
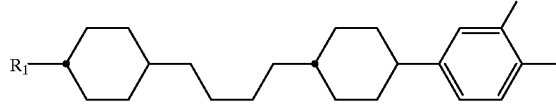
(3-21)
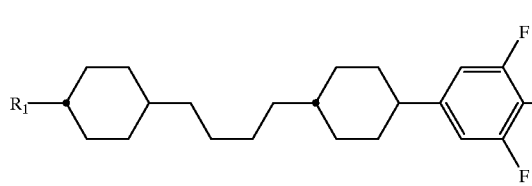
(3-22)
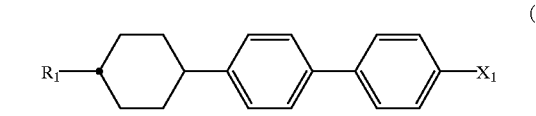
(3-23)
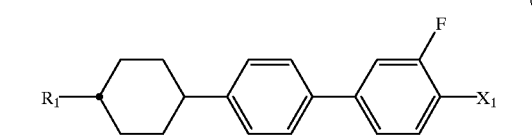
(3-24)
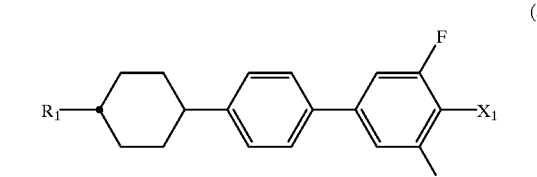
(3-25)
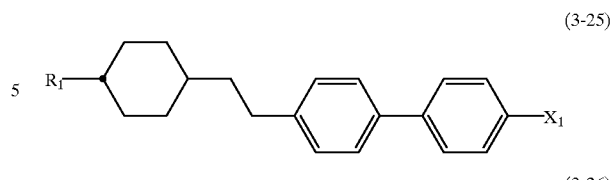
(3-26)
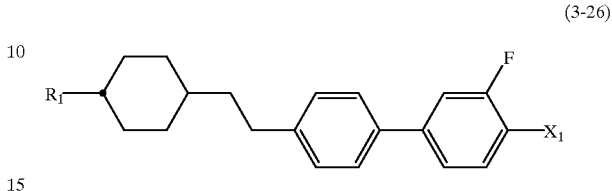
(3-27)
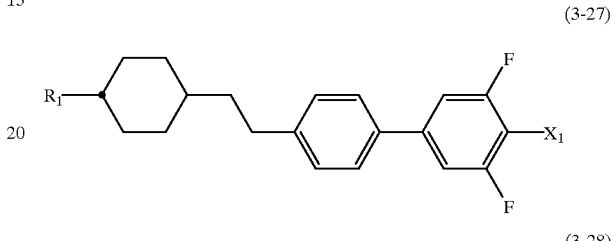
(3-28)
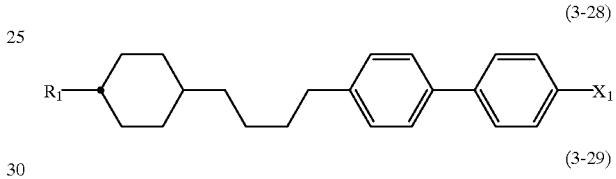
(3-29)
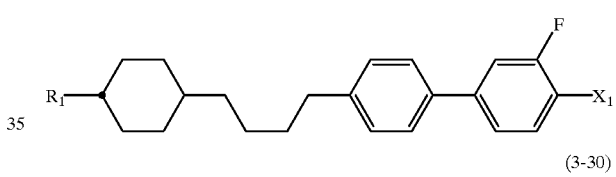
(3-30)
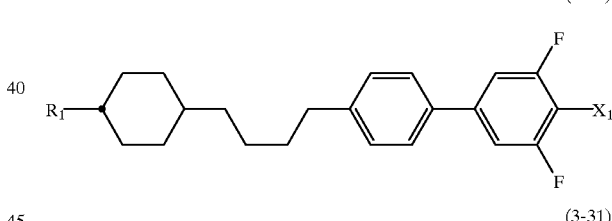
(3-31)
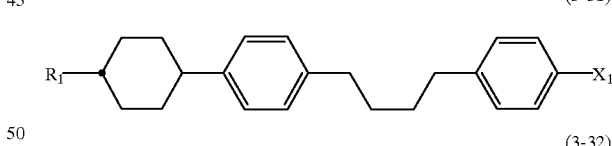
(3-32)
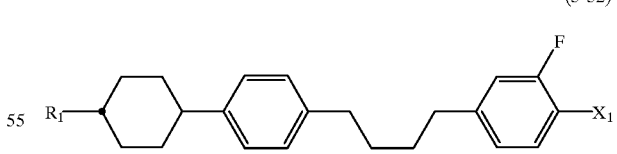
(3-33)
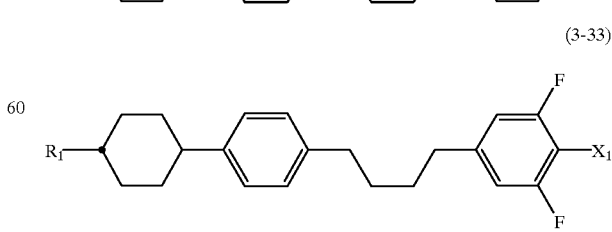

(3-34) 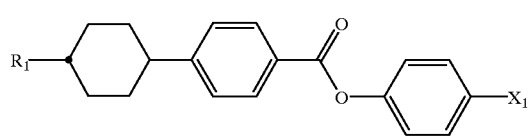
(3-35) 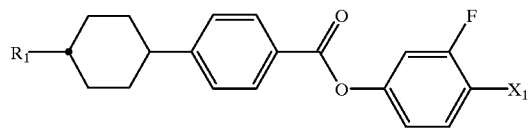
(3-36) 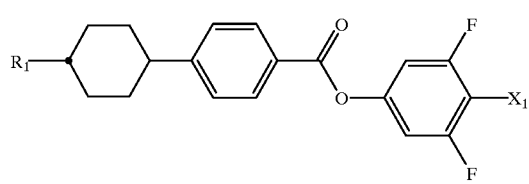
(3-37) 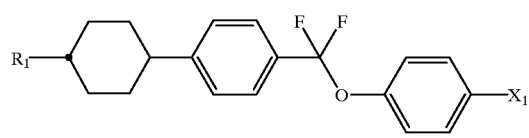
(3-38) 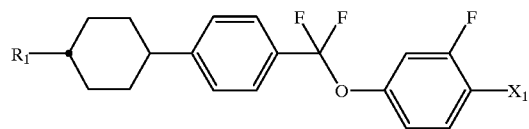
(3-39) 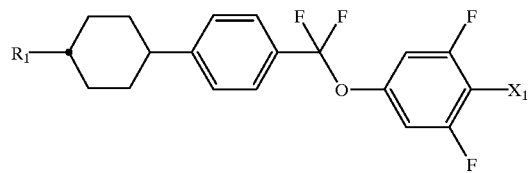
(3-40) 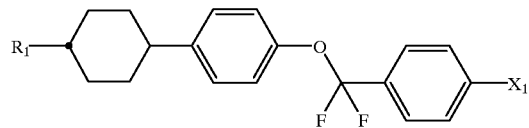
(3-41) 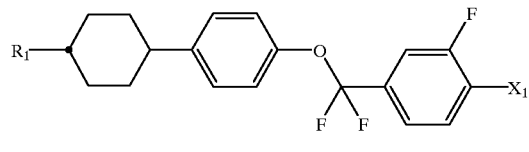
(3-42) 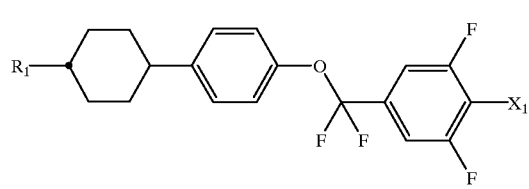
(3-43) 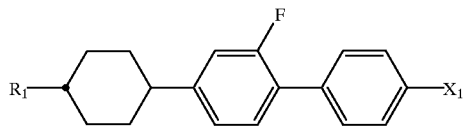
(3-44) 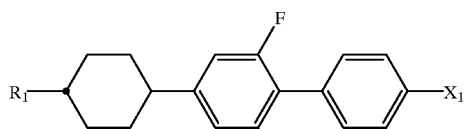
(3-45) 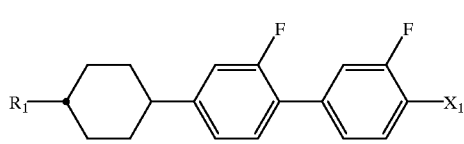
(3-46) 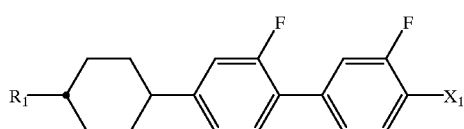
(3-47) 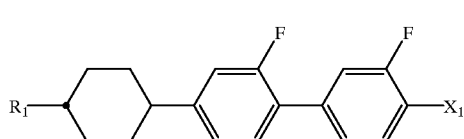
(3-48) 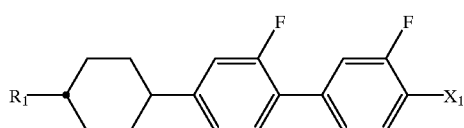
(3-49) 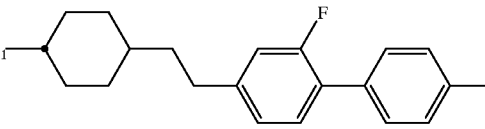
(3-50) 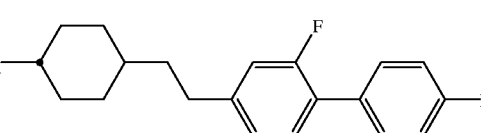
(3-51) 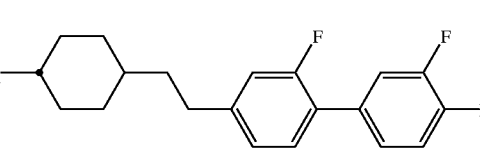

(3-52)
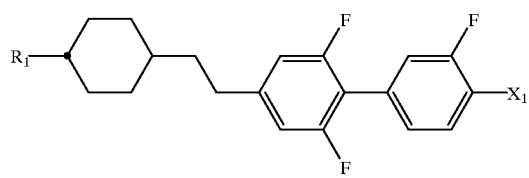
(3-53)
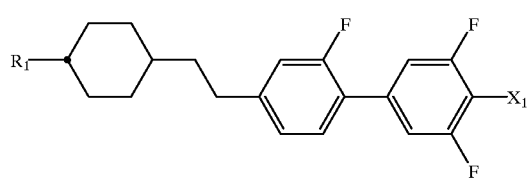
(3-54)
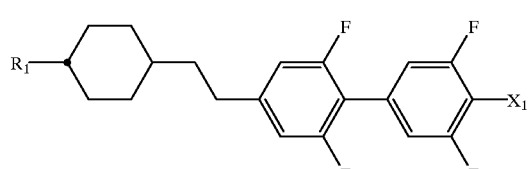
(3-55)
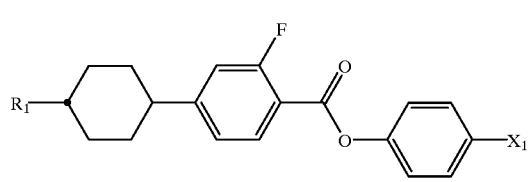
(3-56)
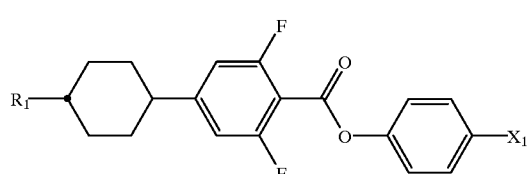
(3-57)
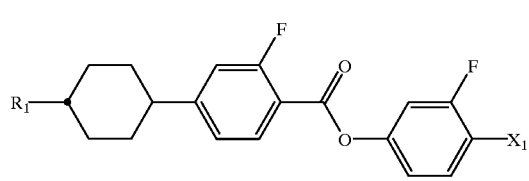
(3-58)
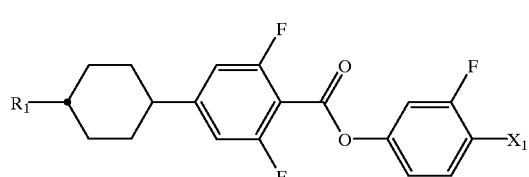
(3-59)
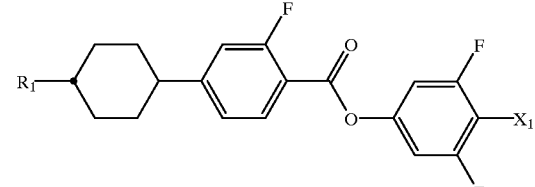
(3-60)
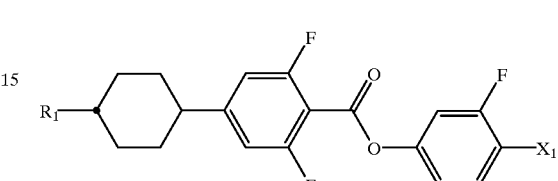
(3-61)
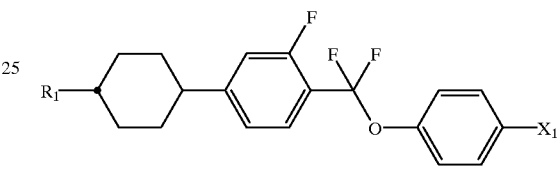
(3-62)
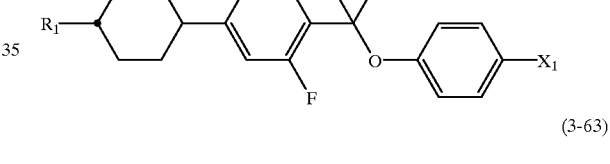
(3-63)
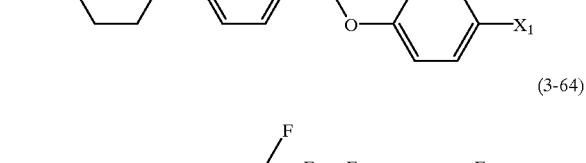
(3-64)
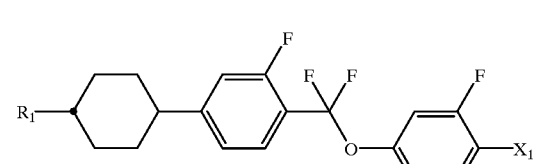
(3-65)
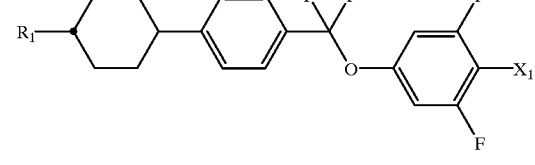

(3-66)
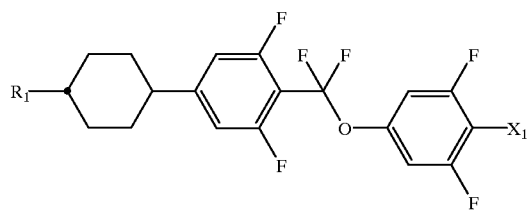
(3-67)
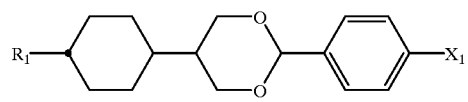
(3-68)
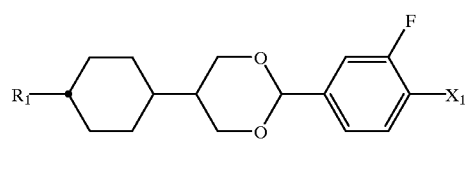
(3-69)
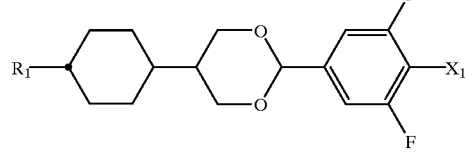
(4-1)
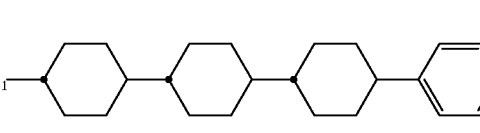
(4-2)
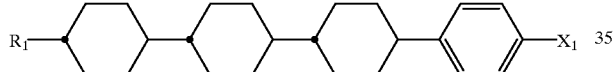
(4-3)
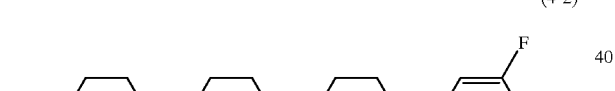
(4-4)
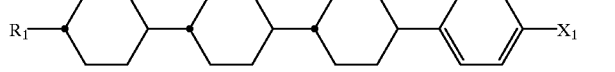
(4-5)
(4-6)
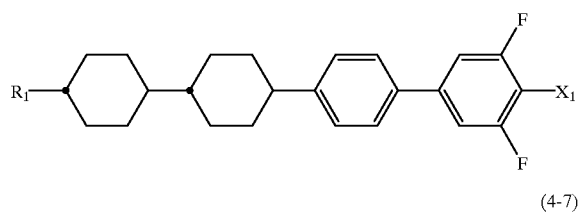
(4-7)
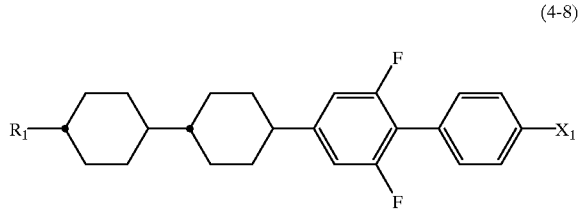
(4-8)
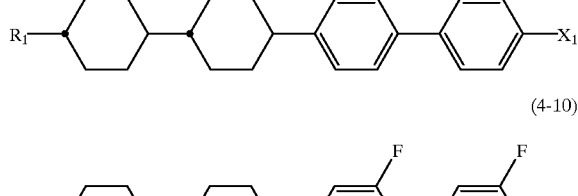
(4-9)
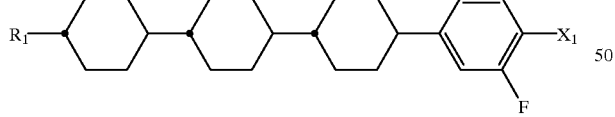
(4-10)
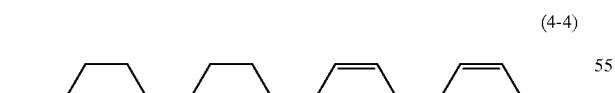
(4-11)
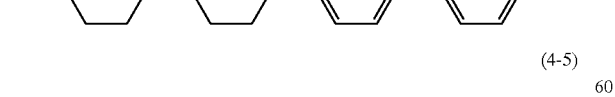
(4-12)
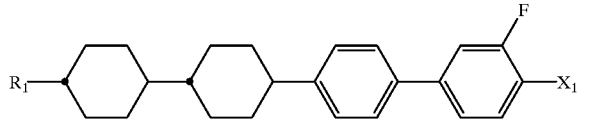
(4-13)
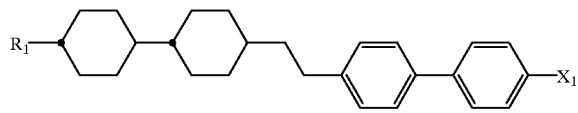

(4-14)
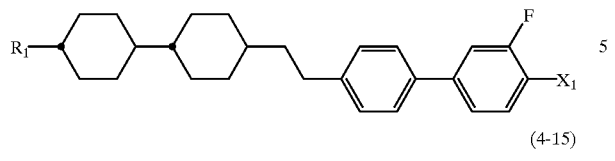

(4-15)
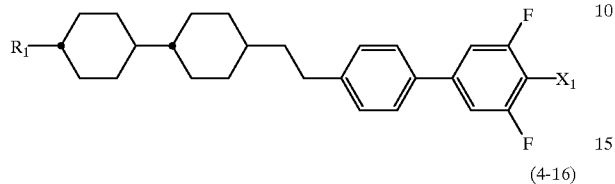

(4-16)
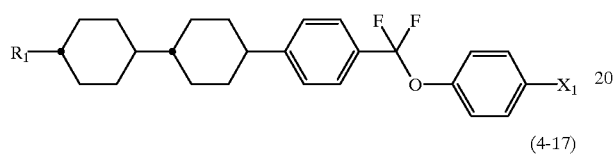

(4-17)
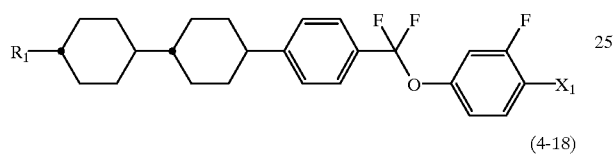

(4-18)
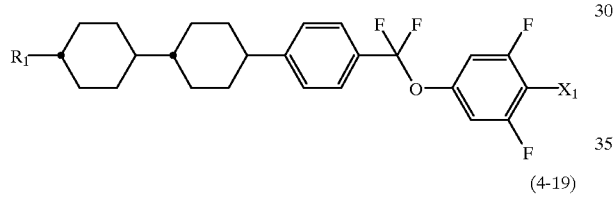

(4-19)
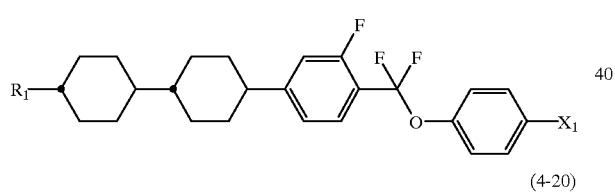

(4-20)
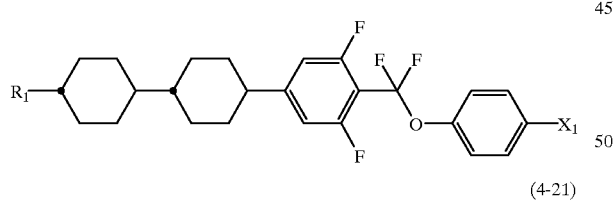

(4-21)
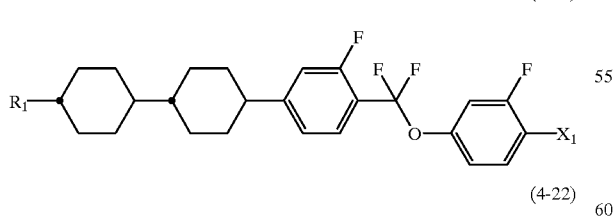

(4-22)
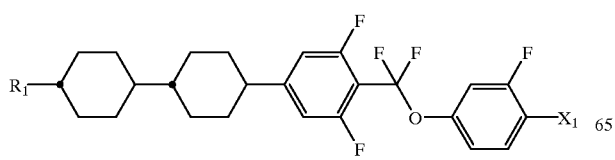

(4-23)
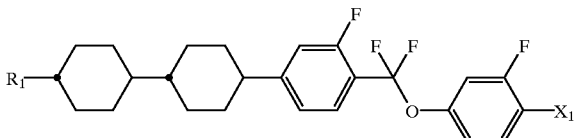

(4-24)
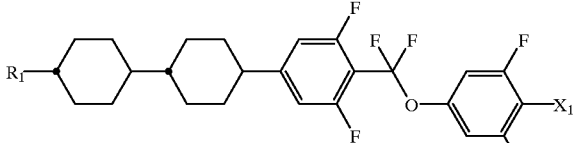

wherein $R_1$ and $X_1$ have the same meaning as described above.

The compounds represented by general formula (2)–(4) have positive dielectric anisotropy values, excellent thermal and chemical stability, and are especially useful for preparing liquid crystal compositions for TFT which require high reliability, i.e. high voltage holding ratio and high specific resistance.

For the preparation of liquid crystal compositions for TFT, the quantities of the compounds represented by general formula (2)–(4) may be within the range of 0.1 to 99.9% by weight, preferably 10 to 97% by weight, and more preferably 40 to 95% by weight relative to the total weight of the liquid crystal composition. The compounds represented by general formula (7)–(9) may further be contained for adjustment of viscosity.

The compounds represented by general formula (2)–(4) may also be used for the preparation of liquid crystal compositions for STN and TN displays. The quantities of the compounds are preferably 50% by weight or less.

As the compounds represented by general formula (5) or (6), the following compounds are preferably used.

(5-1)
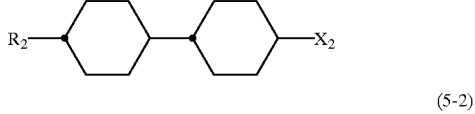

(5-2)
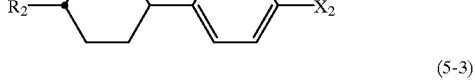

(5-3)
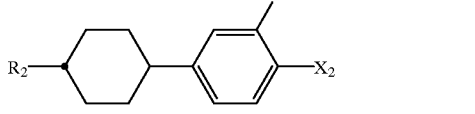

(5-4)
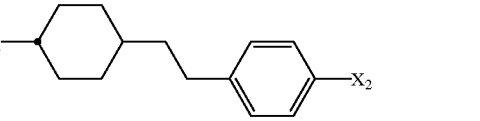

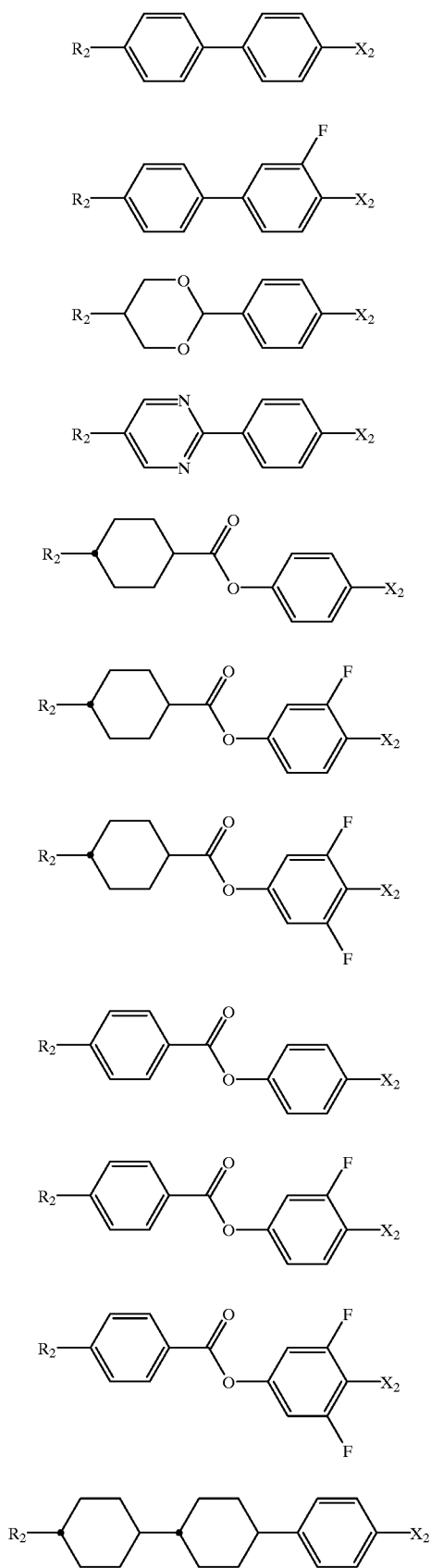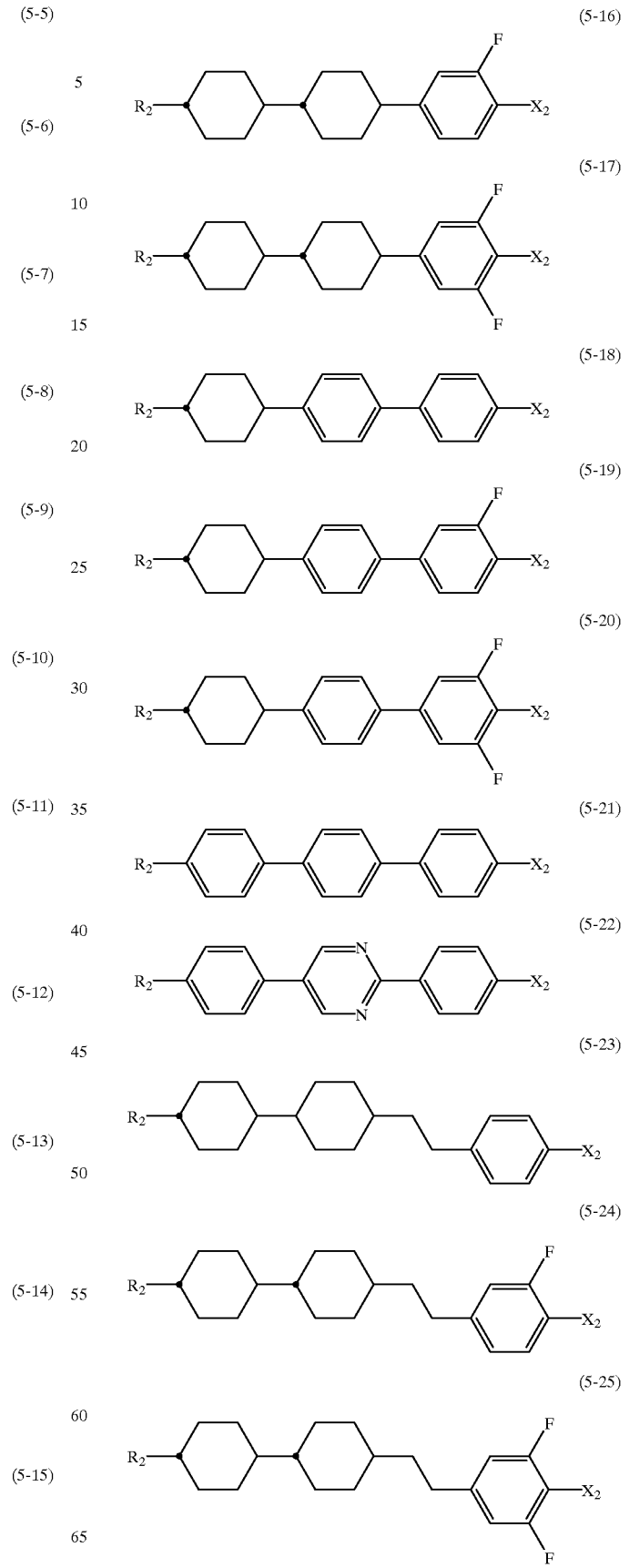

(5-26) 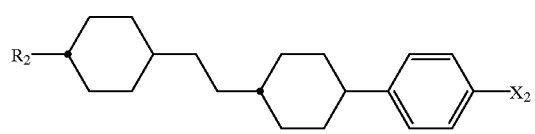
(5-27) 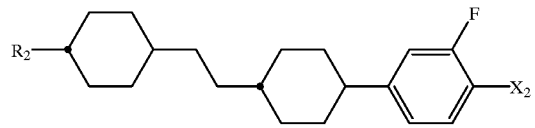
(5-28) 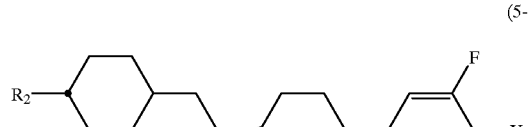
(5-29) 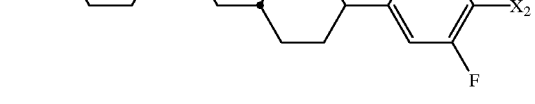
(5-30) 
(5-31) 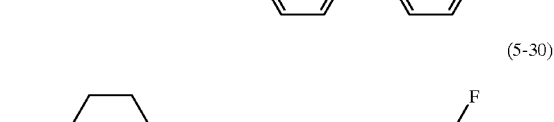
(5-32) 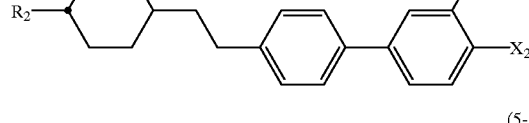
(5-33) 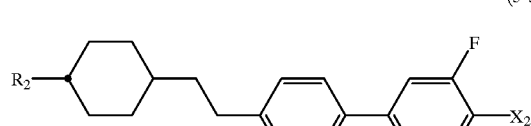
(5-34) 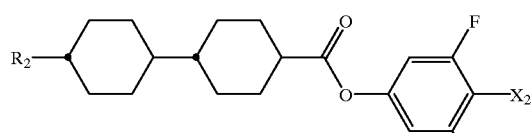
(5-35) 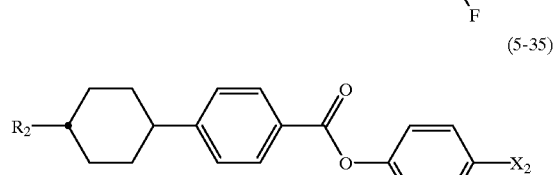
(5-36) 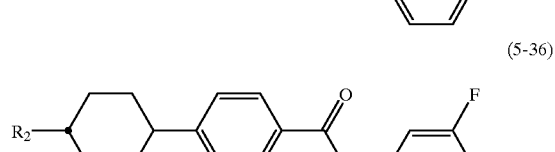
(5-37) 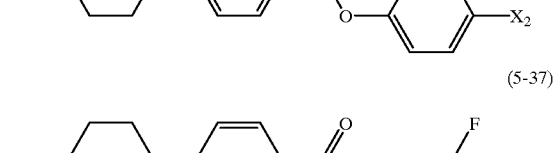
(5-38) 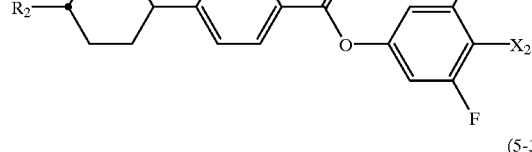
(5-39) 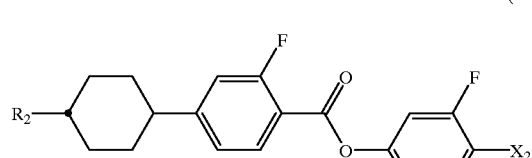
(5-40) 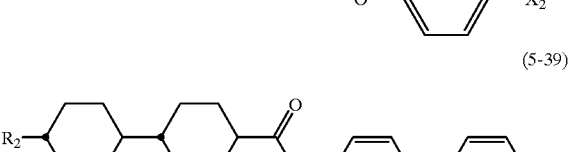
(6-1) 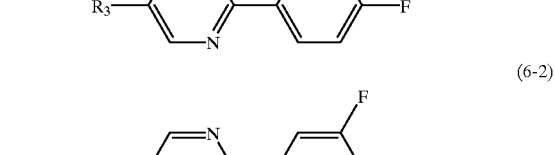
(6-2) 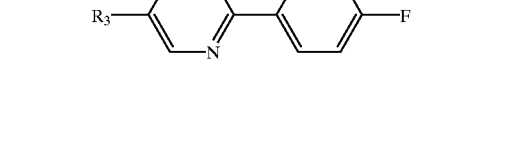

(6-3)

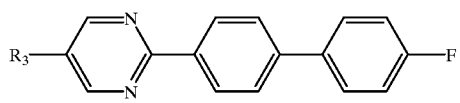

wherein $R_2$, $R_3$ and $X_2$ have the same meaning as shown in the above.

The compounds represented by general formula (5) or (6) have high positive dielectric anisotropy values, and are used especially for lowering the threshold voltage of the liquid crystal composition. The compounds are also used for adjusting optical anisotropy values and expanding the nematic range through, for example, raising clearing points. Further, the compounds are used for improving the sharpness of liquid crystal compositions for STN and TN.

The compounds represented by general formula (5) or (6) are especially useful for preparing liquid crystal compositions for STN and TN.

When the quantity of the compounds represented by general formula (5) or (6) is increased, the threshold voltage of the liquid crystal compositions is lowered and the viscosity is increased. Accordingly, so long as the viscosity of the liquid crystal composition satisfies requirements, use of such compounds in large quantities is advantageous for low-voltage operation. The quantity of the compounds represented by general formula (5) or (6), in case of preparation of liquid crystal compositions for STN or TN, may be within the range of 0.1 to 99.9% by weight, preferably 10–97% by weight, and more preferably 40–95% by weight.

Preferred compounds represented by general formula (7)–(9) may be exemplified below.

(7-1)

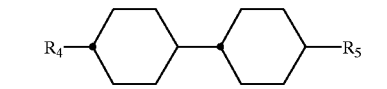

(7-2)

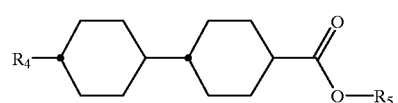

(7-3)

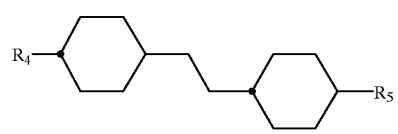

(7-4)

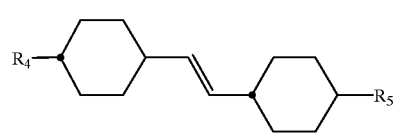

(7-5)

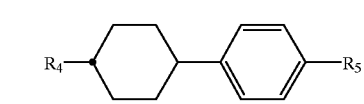

(7-6)

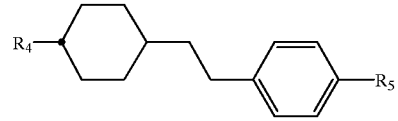

(7-7)

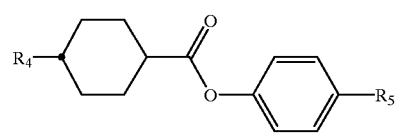

(7-8)

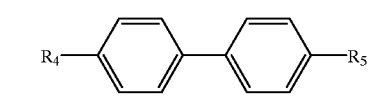

(7-9)

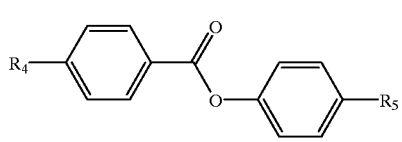

(7-10)

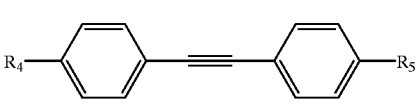

(7-11)

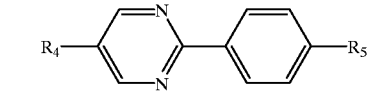

(8-1)

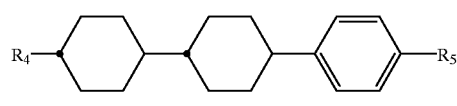

(8-2)

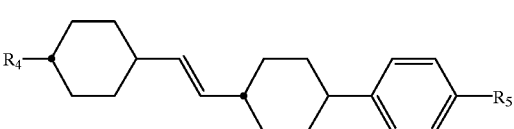

(8-3)

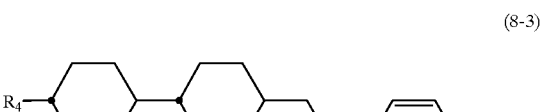

(8-4)

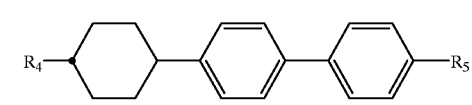

(8-5)

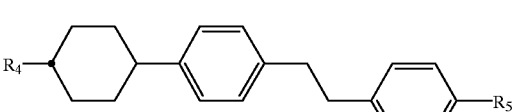

(8-6)
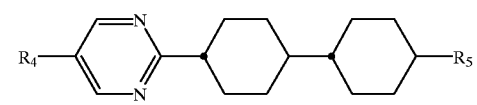

(8-7)
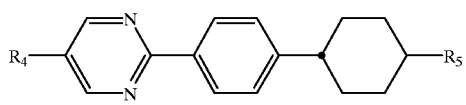

(8-8)
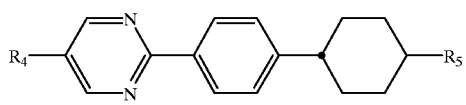

(8-9)
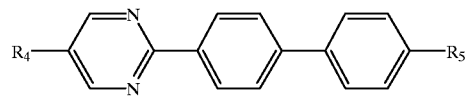

(8-10)
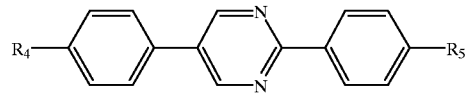

(8-11)
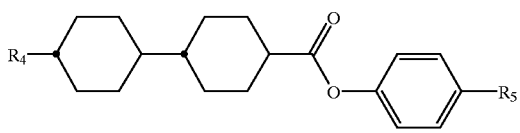

(8-12)
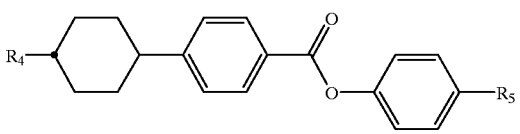

(8-13)
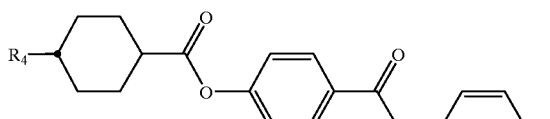

(8-14)
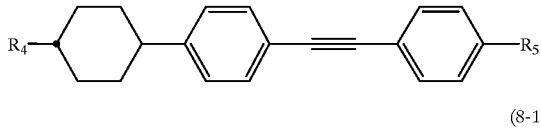

(8-15)
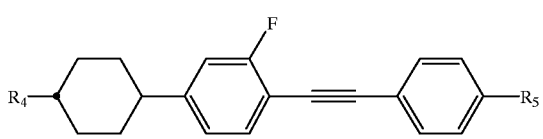

(8-16)
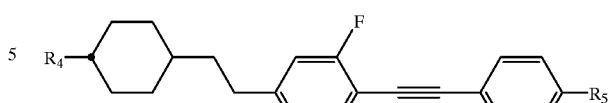

(8-17)
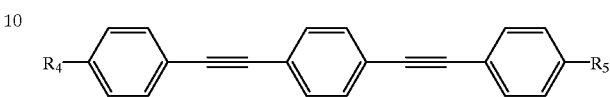

(8-18)
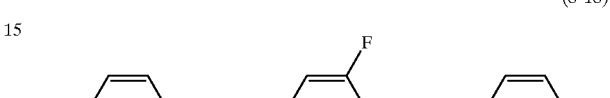

(9-1)
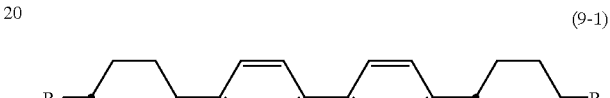

(9-2)
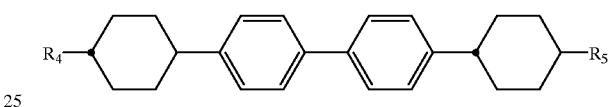

(9-3)
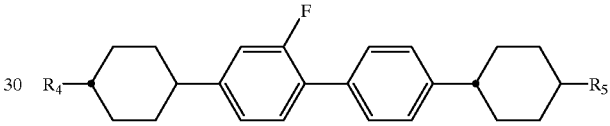

(9-4)
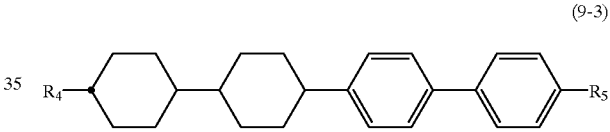

(9-5)
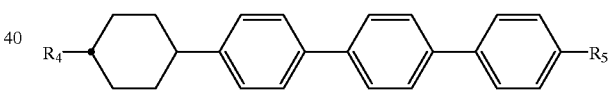

(9-6)
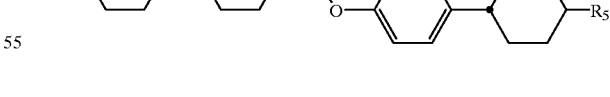

wherein $R_4$ and $R_5$ have the same meaning as described above.

The compounds represented by general formula (7)–(9) have small absolute values of dielectric anisotropy, and these are nearly neutral. The compounds represented by general formula (7) are mainly used for adjusting viscosity and optical anisotropy values. The compounds represented by general formula (8) or (9) aremainlyusedfor expanding the nematic range through, for example, raising clearing points or adjusting optical anisotropy values.

Increase in the quantity of the compounds represented by general formula (7)–(9) increases the threshold voltage and lowers the viscosity of the liquid crystal composition. Therefore, so long as the threshold voltage of the liquid crystal composition satisfies requirements, use of the compounds in large quantities is preferred. The quantity of the compounds represented by general formula (7)–(9), in case of preparation of liquid crystal compositions for TFT, may be 40% by weight or less, preferably 35% by weight or less. In case of preparation of liquid crystal compositions for STN and TN, it may be preferably 70% by weight or less, and more preferably 60% by weight or less.

Moreover, in the present invention, except in special cases such as liquid crystal compositions for an OCB (Optically Compensated Birefringence) mode, an optically active compound is normally added to the liquid crystal composition of the present invention for adjusting required twist angle by inducing formation of the helical structure of the liquid crystal composition, and for preventing reverse twist. Although any known optically active compounds used for the above purposes may be used in the present invention, preferred compounds include the following optically active compounds.

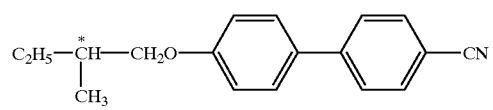
[C15]

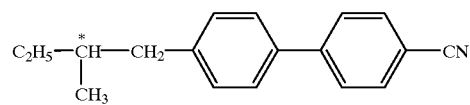
[CB15]

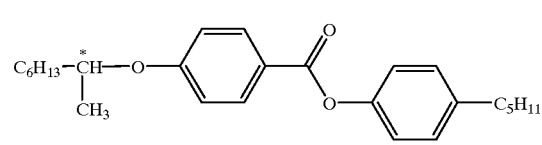
[CM21]

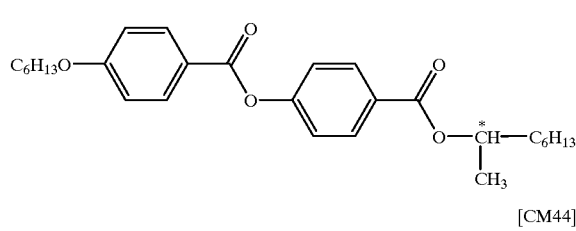
[CM33]

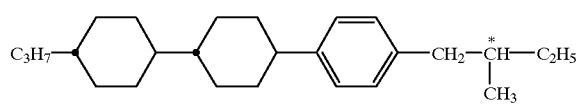
[CM44]

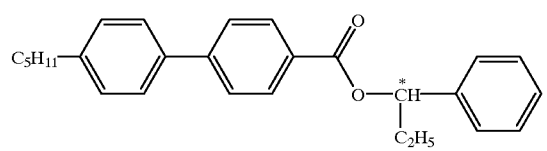
[CM45]

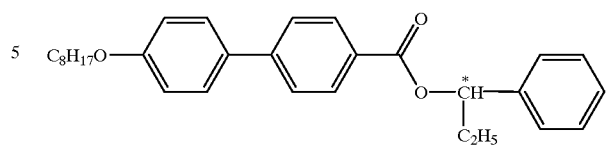
[CM47]

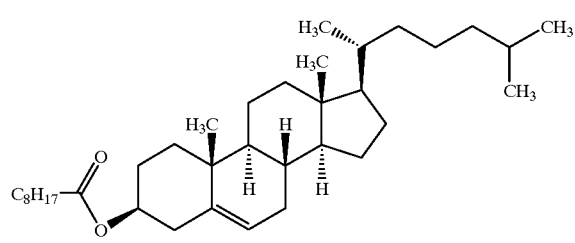
[CN]

In the liquid crystal compositions of the present invention, the pitch of twist is adjusted by addition of these optically active compounds. The pitch of twist is preferably adjusted within the range of 40–200 $\mu$m for liquid crystal compositions for TFT and TN, and 6–20 $\mu$m for liquid crystal compositions for STN. In case of a bistable TN mode, it is preferably adjusted within the range of 1.5–4 $\mu$m. For adjustment of the temperature dependence of the pitch, two or more optically active compounds may be added.

The liquid crystal compositions of the present invention are prepared by well known methods. In general, a method in which various compounds are dissolved in each other at high temperature is used.

Furthermore, the liquid crystal compositions of the present invention may be used as those of the guest-host (GH) mode by adding dichroic dyes such as merocyanine, styryl, azo, azomethyne, azoxy, quinophthalone, anthraquinone and tetrazine types. Moreover, the compositions may be used for NCAP, which is prepared by microcapsulation of a nematic liquid crystal, or for a polymer dispersion liquid crystal display device (PDLCD) represented by a polymer network liquid crystal display device (PNLCD), which is prepared by making a polymer of tridimensional network structure in liquid crystal. In addition, the liquid crystal compositions may be used for an electrically controlled birefringence (ECB) mode or a dynamic scattering (DS) mode.

The following liquid crystal compositions containing the compounds of the present invention can be exemplified. Moreover, the compounds in the composition examples and undermentioned working examples are represented in accordance with the following rule by brief symbols, and the numbers of the compounds are the same as those in the following examples. Further, in the composition examples and working examples, except previous notice, "%" means "% by weight".

| Rc-Aa-Za~~~~~~Zn-Ac-Rd | |
|---|---|
| Left end group Rc | |
| $C_aH_{2a+1}-$ | a- |
| $C_aH_{2a+1}O-$ | aO- |
| $C_aH_{2a+1}OC_bH_{2b}-$ | aOb— |
| $C_aH_{2a+1}OC_bH_{2b}O-$ | aObO— |

-continued

| Rc-Aa-Za~---~---~Zn-Ac-Rd | |
|---|---|
| $C_{a-1}H_{2(a-1)+1}C(C_bH_{2b+1})HC_cH_{2c}-$ | a(b)c- |
| $CFH_2C_{a-1}H_{2(a-1)}-$ | Fa- |
| $CF_2HC_{a-1}H_{2(a-1)}-$ | FFa- |
| $CF_3C_{a-1}H_{2(a-1)}-$ | FFFa- |
| $CFH_2C_{a-1}H_{2(a-1)}O-$ | FaO- |
| $CFH_2C_{a-1}H_{2(a-1)}OC_bH_{2b}-$ | FaOb- |
| $C_aH_{2a+1}CFHC_bH_{2b}-$ | a(f)b- |
| $C_aH_{2a+1}CF_2C_bH_{2b}-$ | a(FF)b- |
| $C_aH_{2a+1}CH=CHC_bH_{2b}-$ | aVb- |
| $C_aH_{2a+1}CH=CHC_bH_{2b}CH=CHC_cH_{2c}-$ | aVbVc- |
| $C_aH_{2a+1}CH=CHC_bH_{2b}OC_cH_{2c}-$ | aVbOc- |
| $C_aH_{2a+1}OC_bH_{2b}CH=CHC_cH_{2c}-$ | aObVc- |
| $CFH_2C_{a-1}H_{2(a-1)}CH=CHC_bH_{2b}-$ | FaVb- |
| $FFC=CHC_aH_{2a}-$ | FFVa- |
| $F(CN)C=CHC_aH_{2a}-$ | FCVa- |

Bonding group Za~Zn

| | |
|---|---|
| $-(CH_2)_a-$ | a |
| $-CH_2O-$ | $CH_2O$ |
| $-OCH_2-$ | $OCH_2$ |
| $-C_3H_6O-$ | $C_3H_6O$ |
| $-OC_3H_6-$ | $OC_3H_6$ |
| $-COO-$ | E |
| $-C\equiv C-$ | T |
| $-CH=CH-$ | V |
| $-CF_2O-$ | $CF_2O$ |
| $-OCF_2-$ | $OCF_2$ |

Ring structure Aa~Ao

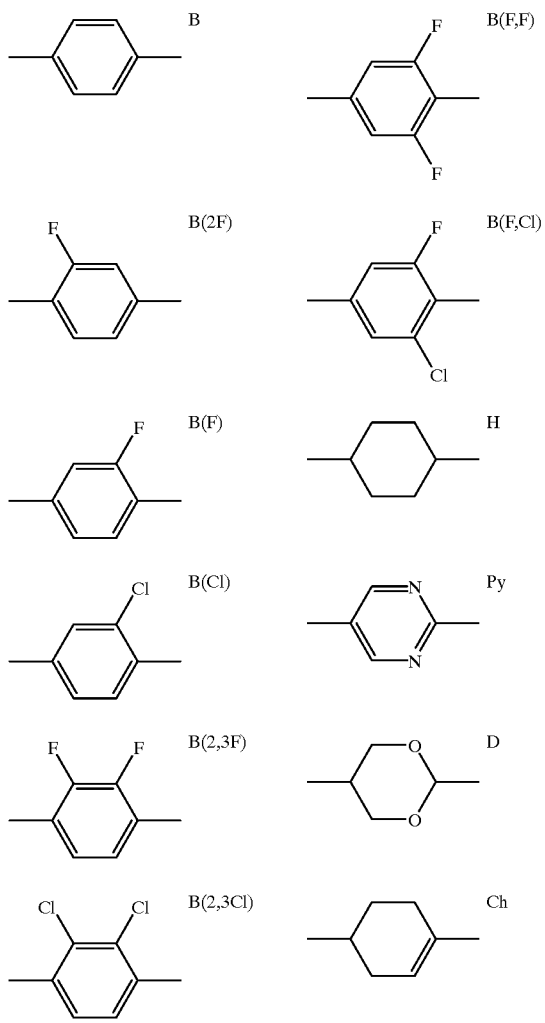

-continued

| Rc-Aa-Za~---~---~Zn-Ac-Rd | |
|---|---|
| Right end group Rd | |
| —F | —F |
| —Cl | —CL |
| —CN | —C |
| —$CF_3$ | —CF3 |
| —$OCF_3$ | —OCF3 |
| —$OCF_2H$ | —OCF2H |
| —$OCF_2CF_2H$ | —OCF2CF2H |
| —$OCF_2CFHCF_2$ | —OCF2CFHCF3 |
| —$C_wH_{2w+1}$ | -w |
| —$OC_wH_{2w+1}$ | —Ow |
| —$C_wH_{2w}CH=CH_2$ | -wV |
| —$C_wH_{2w}CH=CHC_xH_{2x+1}$ | -wVx |
| —$COOCH_3$ | -EMe |
| —$C_wH_{2w}CH+CHC_xH_{2x}F$ | -wVxF |
| —$CH=CF_2$ | -VFF |
| —$C_wH_{2w}CH=CF_2$ | -wVFF |
| —$C\equiv C-CN$ | -TC |

Furthermore, for example, in the following partial structural formula, when the hydrogen atom of trans-1,4-cyclohexylene is substituted by a heavy hydrogen atom (D) at the positions of $Q_.$, $Q$, and $Q_3$, it is represented by a symbol H[1D, 2D, 3D], and when the hydrogen atom is substituted by a heavy hydrogen atom at the positions of $Q_5$, $Q_6$ and $Q_7$, it is represented by a symbol H[5D, 6D, 7D].

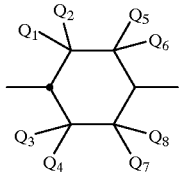

Composition Example 1

| | | |
|---|---|---|
| F5-B(F)B(F,F)B(F)—$OCF_3$ | (Compound No.1) | 5.0% |
| F5-B(F)2B(F,F)B(F)—CL | (Compound No.79) | 5.0% |
| 1V2-BEB(F,F)—C | | 5.0% |
| 3-HB—C | | 20.0% |
| 2-BTB-1 | | 10.0% |
| 3-HH-4 | | 11.0% |
| 3-HHB-1 | | 11.0% |
| 3-HHB-3 | | 9.0% |
| 3-H2BTB-2 | | 4.0% |
| 3-H2BTB-3 | | 4.0% |
| 3-H2BTB-4 | | 4.0% |
| 3-HB(F)TB-2 | | 6.0% |
| 3-HB(F)TB-3 | | 6.0% |
| CM33 | | 0.8 parts |

Composition Example 2

| | | |
|---|---|---|
| F2-BB(F)2B(F,F)—$CF_3$ | (Compound No.89) | 5.0% |
| FF3-B(F)B(F)B(F)—F | (Compound No.15) | 3.0% |
| V2-HB—C | | 12.0% |
| 1V2-HB—C | | 12.0% |
| 3-HB—C | | 10.0% |
| 3-H[1D,2D,3D]-C | | 9.0% |
| 3-HB(F)—C | | 5.0% |
| 2-BTB-1 | | 2.0% |
| 3-HH-4 | | 8.0% |
| 3-HH—VFF | | 6.0% |
| 2-H[1D,2D,3D]HB—C | | 3.0% |
| 3-HHB—C | | 3.0% |
| 3-HB(F)TB-2 | | 8.0% |
| 3-H2BTB-2 | | 5.0% |
| 3-H2BTB-3 | | 5.0% |

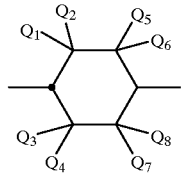

| | | |
|---|---|---|
| 3-H2BTB-4 | | 4.0% |
| Composition Example 3 | | |
| F4-B2B(F,F)B(F)—OCF₃ | (Compound No.89) | 5.0% |
| F3-B(F,F)B(F)BCL | (Compound No.9) | 4.0% |
| 301-BEB(F)—C | | 15.0% |
| 401-BEB(F)—C | | 13.0% |
| 501-BEB(F)—C | | 13.0% |
| 2-HHB(F)—C | | 15.0% |
| 3-HHB(F)—C | | 15.0% |
| 3-HB(F)TB-2 | | 4.0% |
| 3-HB(F)TB-3 | | 4.0% |
| 3-HHB-1 | | 8.0% |
| 3-HHB-01 | | 4.0% |
| Composition Example 4 | | |
| F5-B(F)B(F,F)B(F)—OCF₃ | (Compound No.1) | 5.0% |
| 2(F)1-BB(F)B(F)—CF₃ | (Compound No.7) | 2.0% |
| 1(FF)3-BB(F)B(F,F)—OCF₃ | (Compound No.13) | 4.0% |
| 5-PyB—F | | 4.0% |
| 3-PyB(F)—F | | 4.0% |
| 2-BB—C | | 5.0% |
| 5-BB—C | | 5.0% |
| 2-PyB-2 | | 2.0% |
| 3-PyB-2 | | 2.0% |
| 6-PyB-05 | | 3.0% |
| 6-PyB-06 | | 3.0% |
| 6-PyB-07 | | 3.0% |
| 3-PyBB—F | | 6.0% |
| 4-PyBB—F | | 6.0% |
| 5-PyBB—F | | 6.0% |
| 3-HHB-1 | | 4.0% |
| 3-HHB-3 | | 8.0% |
| 2-H2BTB-2 | | 4.0% |
| 2-H2BTB-3 | | 4.0% |
| 2-H2BTB-4 | | 5.0% |
| 3-H2BTB-2 | | 5.0% |
| 3-H2BTB-3 | | 5.0% |
| 3-H2BTB-4 | | 5.0% |
| Composition Example 5 | | |
| F5-B(F)2B(F,F)B(F)—CL | (Compound No.79) | 4.0% |
| F4-B2B(F,F)B(F)—OCF₃ | (Compound No.89) | 2.0% |
| F2-BB(F)2B(F,F)—CF₃ | (Compound No.115) | 2.0% |
| 3-DB—C | | 10.0% |
| 4-DB—C | | 10.0% |
| 2-BEB—C | | 12.0% |
| 3-PyB(F)—F | | 6.0% |
| 3-HEB-04 | | 8.0% |
| 4-HEB-02 | | 6.0% |
| 5-HEB-01 | | 6.0% |
| 3-HEB-02 | | 5.0% |
| 5-HEB-5 | | 5.0% |
| 4-HEB-5 | | 5.0% |
| 10-BEB-2 | | 4.0% |
| 3-HHB-1 | | 6.0% |
| 3-HHEBB—C | | 3.0% |
| 3-HBEBB—C | | 3.0% |
| 5-HBEBB—C | | 3.0% |
| Composition Example 6 | | |
| F5-B(F)B(F,F)B(F)—OCF₃ | (Compound No.1) | 8.0% |
| F5-B(F)2B(F,F)B(F)—CL | (Compound No.79) | 4.0% |
| FF3-B(F)B(F)B(F)—F | (Compound No.15) | 4.0% |
| 3-HB—C | | 10.0% |
| 7-HB—C | | 3.0% |
| 101-HB—C | | 10.0% |
| 3-HB(F)—C | | 10.0% |

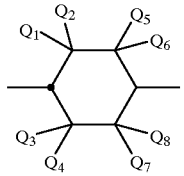

| | | |
|---|---|---|
| 2-PyB-2 | | 2.0% |
| 3-PyB-2 | | 2.0% |
| 4-PyB-2 | | 2.0% |
| 101-HH-3 | | 7.0% |
| 2-BTB-01 | | 7.0% |
| 3-HHB-1 | | 7.0% |
| 3-HHB—F | | 4.0% |
| 3-HHB-01 | | 4.0% |
| 3-H2BTB-2 | | 3.0% |
| 3-H2BTB-3 | | 3.0% |
| 2-PyBH-3 | | 4.0% |
| 3-PyBH-3 | | 3.0% |
| 3-PyBB-2 | | 3.0% |
| Composition Example 7 | | |
| F5-B(F)2B(F,F)B(F)—CL | (Compound No.79) | 4.0% |
| F3-B(F,F)B(F)B—CL | (Compound No.9) | 3.0% |
| 201-BEB(F)—C | | 5.0% |
| 301-BEB(F)—C | | 12.0% |
| 1V2-BEB(F,F)—C | | 10.0% |
| 3-HH-EMe | | 10.0% |
| 3-HB-02 | | 18.0% |
| 7-HEB—F | | 2.0% |
| 3-HHEB—F | | 2.0% |
| 5-HHEB—F | | 2.0% |
| 3-HBEB—F | | 4.0% |
| 201-HBEB(F)—C | | 2.0% |
| 3-HB(F)EB(F)—C | | 2.0% |
| 3-HBEB(F,F)—C | | 2.0% |
| 3-HHB—F | | 4.0% |
| 3-HHB-01 | | 4.0% |
| 3-HHB-3 | | 10.0% |
| 3-HEBEB—F | | 2.0% |
| 3-HEBEB-1 | | 2.0% |
| Composition Example 8 | | |
| F5-B(F)B(F,F)B(F)—OCF₃ | (Compound No.1) | 3.0% |
| F5-B(F)2B(F,F)B(F)—CL | (Compound No.79) | 3.0% |
| 5-BEB(F)—C | | 5.0% |
| V—HB—C | | 11.0% |
| 5-PyB—C | | 6.0% |
| 4-BB-3 | | 11.0% |
| 3-HH-2V | | 10.0% |
| 5-HH—V | | 11.0% |
| V—HHB-1 | | 7.0% |
| V2-HHB-1 | | 15.0% |
| 3-HHB-1 | | 3.0% |
| 1V2-HBB-2 | | 10.0% |
| 3-HHEBH-3 | | 5.0% |
| Composition Example 9 | | |
| FF3-B(F)B(F)B(F)—F | (Compound No.15) | 4.0% |
| F5-B(F)2B(F,F)B(F)—CL | (Compound No.79) | 4.0% |
| F3-B(F,F)B(F)B—CL | (Compound No.9) | 4.0% |
| 201-BEB(F)—C | | 5.0% |
| 301-BEB(F)—C | | 12.0% |
| 1V2-BEB(F,F)—C | | 16.0% |
| 3-HB-02 | | 10.0% |
| 3-HH-4 | | 3.0% |
| 3-HHB-F | | 3.0% |
| 3-HHB-1 | | 4.0% |
| 3-HHB-01 | | 4.0% |
| 3-HBEB—F | | 4.0% |
| 3-HHEB—F | | 7.0% |
| 5-HHEB—F | | 7.0% |
| 3-H2BTB-2 | | 4.0% |
| 3-H2BTB-3 | | 4.0% |
| 3-HB(F)TB-2 | | 5.0% |

-continued

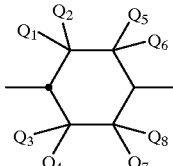

Composition Example 10

| | | |
|---|---|---|
| F5-B(F)B(F,F)B(F)—OCF₃ | (Compound No.1) | 8.0% |
| F4-B2B(F,F)B(F)—OCF₃ | (Compound No.89) | 3.0% |
| F2-BB(F)2B(F,F)—CF₃ | (Compound No.115) | 2.0% |
| 2-BEB—C | | 12.0% |
| 3-BEB—C | | 4.0% |
| 4-BEB—C | | 6.0% |
| 3-HB—C | | 20.0% |
| 3-HEB-04 | | 12.0% |
| 4-HEB-02 | | 8.0% |
| 5-HEB-01 | | 8.0% |
| 3-HEB-02 | | 6.0% |
| 3-HHB-1 | | 7.0% |
| 3-HHB-01 | | 4.0% |

Composition Example 11

| | | |
|---|---|---|
| F5-B(F)B(F,F)B(F)—OCF₃ | (Compound No.1) | 7.0% |
| F3-B(F,F)B(F)B—CL | (Compound No. 9) | 3.0% |
| F2-BB(F)2B(F,F)—CF₃ | (Compound No.115) | 3.0% |
| 2-BEB—C | | 10.0% |
| 5-BB—C | | 12.0% |
| 7-BB—C | | 7.0% |
| 2-BTB-1 | | 10.0% |
| 10-BEB-2 | | 10.0% |
| 10-BEB-5 | | 12.0% |
| 2-HHB-1 | | 4.0% |
| 3-HHB—F | | 4.0% |
| 3-HHB-1 | | 7.0% |
| 3-HHB-01 | | 4.0% |
| 3-HHB-3 | | 7.0% |

Composition Example 12

| | | |
|---|---|---|
| F3-B(F,F)B(F)B—CL | (Compound No.9) | 6.0% |
| 2(F)1-BB(F)B(F)—CF₃ | (Compound No.7) | 6.0% |
| 1V2-BEB(F,F)—C | | 10.0% |
| 3-HB—C | | 10.0% |
| V2V—HB—C | | 14.0% |
| V2V—HH-3 | | 19.0% |
| 3-HB-02 | | 4.0% |
| 3-HHB-1 | | 10.0% |
| 3-HHB-3 | | 5.0% |
| 3-HB(F)TB-2 | | 4.0% |
| 3-HB(F)TB-3 | | 4.0% |
| 3-H2BTB-2 | | 4.0% |
| 3-H2BTB-3 | | 4.0% |

Composition Example 13

| | | |
|---|---|---|
| F5-B(F)B(F,F)B(F)—OCF₃ | (Compound No.1) | 3.0% |
| F4-B2B(F,F)B(F)—OCF₃ | (Compound No.89) | 3.0% |
| 2(F)1-BB(F)B(F)—CF₃ | (Compound No.7) | 3.0% |
| 1(FF)3-BB(F)B(F,F)—OCF₃ | (Compound No.13) | 2.0% |
| 5-BTB(F)TB-3 | | 10.0% |
| V2-HB-TC | | 10.0% |
| 3-HB-TC | | 10.0% |
| 3-HB—C | | 10.0% |
| 5-HB—C | | 7.0% |
| 5-BB—C | | 3.0% |
| 2-BTB-1 | | 10.0% |
| 2-BTB-01 | | 5.0% |
| 3-HH-4 | | 5.0% |
| 3-HHB-1 | | 10.0% |
| 3-H2BTB-2 | | 3.0% |
| 3-H2BTB-3 | | 3.0% |
| 3-HB(F)TB-2 | | 3.0% |

Composition Example 14

| | | |
|---|---|---|
| FF3-B(F)B(F)B(F)—F | (Compound No.15) | 4.0% |

-continued

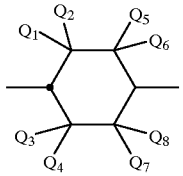

| | | |
|---|---|---|
| 1V2-BEB(F,F)—C | | 6.0% |
| 3-HB—C | | 18.0% |
| 2-BTB-1 | | 10.0% |
| 5-HH—VFF | | 30.0% |
| 1-BHH—VFF | | 8.0% |
| 1-BHH-2VFF | | 11.0% |
| 3-H2BTB-2 | | 5.0% |
| 3-H2BTB-3 | | 4.0% |
| 3-HHB-1 | | 4.0% |

Composition Example 15

| | | |
|---|---|---|
| F3-B(F,F)B(F)B—CL | (Compound No.9) | 7.0% |
| FF3-B(F)B(F)B(F)—F | (Compound No.15) | 7.0% |
| 2-HB—C | | 5.0% |
| 3-HB—C | | 12.0% |
| 3-HB-02 | | 15.0% |
| 2-BTB-1 | | 3.0% |
| 3-HHB-1 | | 8.0% |
| 3-HHB—F | | 4.0% |
| 3-HHB-01 | | 5.0% |
| 3-HHEB—F | | 4.0% |
| 5-HHEB—F | | 4.0% |
| 2-HHB(F)—F | | 7.0% |
| 3-HHB(F)—F | | 7.0% |
| 5-HHB(F)—F | | 7.0% |
| 3-HHB(F,F)—F | | 5.0% |

Composition Example 16

| | | |
|---|---|---|
| F5-B(F)B(F,F)B(F)—OCF₃ | (Compound No.1) | 7.0% |
| F5-B(F)2B(F,F)B(F)—CL | (Compound No.79) | 6.0% |
| 2-HHB(F)—F | | 17.0% |
| 3-HHB(F)—F | | 17.0% |
| 5-HHB(F)—F | | 16.0% |
| 2-H2HB(F)—F | | 10.0% |
| 3-H2HB(F)—F | | 5.0% |
| 5-H2HB(F)—F | | 10.0% |
| 2-HBB(F)—F | | 6.0% |
| 3-HBB(F)—F | | 6.0% |
| CN | | 0.3% |

Composition Example 17

| | | |
|---|---|---|
| FF3-B(F)B(F)B(F)—F | (Compound No.15) | 5.0% |
| 1(FF)3-BB(F)B(F,F)—OCF₃ | (Compound No.13) | 5.0% |
| F5-B(F)B(F,F)B(F)—OCF₃ | (Compound No.1) | 3.0% |
| F3-B(F,F)B(F)B—CL | (Compound No.9) | 3.0% |
| F4-B2B(F,F)B(F)—OCF₃ | (Compound No.89) | 4.0% |
| 3-HB-02 | | 10.0% |
| 3-HH-4 | | 2.0% |
| 3-HH[5D,6D,7D]-4 | | 3.0% |
| 2-HHB(F)—F | | 10.0% |
| 3-HHB(F)—F | | 10.0% |
| 5-HH[5D,6D,7D]B(F)—F | | 10.0% |
| 3-H2HB(F)—F | | 5.0% |
| 2-HBB(F)—F | | 3.0% |
| 3-HBB(F)—F | | 3.0% |
| 2-H2BB(F)—F | | 5.0% |
| 3-H2BB(F)—F | | 6.0% |
| 3-HHB-1 | | 8.0% |
| 3-HHB-01 | | 5.0% |

Composition Example 18

| | | |
|---|---|---|
| F5-B(F)B(F,F)B(F)—OCF₃ | (Compound No.1) | 4.0% |
| F5-B(F)2B(F,F)B(F)—CL | (Compound No.79) | 4.0% |
| F4-B2B(F,F)B(F)—OCF₃ | (Compound No.89) | 4.0% |
| FF3-B(F)B(F)B(F)—F | (Compound No.15) | 4.0% |
| 7-HB(F,F)—F | | 3.0% |
| 3-HB-02 | | 7.0% |
| 2-HHB(F)—F | | 10.0% |

-continued

[Structure diagram with Q1-Q8 labels on hexagonal ring]

| | | |
|---|---|---|
| 3-HHB(F)—F | | 10.0% |
| 5-HHB(F)—F | | 10.0% |
| 2-HBB(F)—F | | 9.0% |
| 3-HBB(F)—F | | 9.0% |
| 2-HBB—F | | 4.0% |
| 3-HBB—F | | 4.0% |
| 5-HBB—F | | 3.0% |
| 5-HBB(F,F)—F | | 5.0% |
| 3-HBB(F,F)—F | | 10.0% |
| Composition Example 19 | | |
| 2(F)1-BB(F)B—CF₃ | (Compound No.7) | 5.0% |
| 1(FF)3-BB(F)B(F,F)—OCF₃ | (Compound No.13) | 5.0% |
| 7-HB(F,F)—F | | 3.0% |
| 3-H2HB(F,F)—F | | 12.0% |
| 4-H2HB(F,F)—F | | 10.0% |
| 3-HHB(F,F)—F | | 5.0% |
| 4-HHB(F,F)—F | | 5.0% |
| 3-H2BB(F,F)—F | | 15.0% |
| 5-H2BB(F,F)—F | | 10.0% |
| 3-HBB(F,F)—F | | 12.0% |
| 5-HBB(F,F)—F | | 12.0% |
| 3-HBCF2OB(F,F)—F | | 6.0% |
| Composition Example 20 | | |
| F5-B(F)B(F,F)B(F)—OCF₃ | (Compound No.1) | 5.0% |
| F2-BB(F)2B(F,F)—CF₃ | (Compound No.115) | 3.0% |
| F3-B(F,F)B(F)B—CL | (Compound No.9) | 3.0% |
| 7-HB(F,F)—F | | 5.0% |
| 3-H2HB(F,F)—F | | 12.0% |
| 4-H2HB(F,F)—F | | 10.0% |
| 3-HHB(F)—F | | 10.0% |
| 3-HBB(F)—F | | 10.0% |
| 3-HHEB(F,F)—F | | 10.0% |
| 2-HBEB(F,F)—F | | 3.0% |
| 3-HBEB(F,F)—F | | 5.0% |
| 5-HBEB(F,F)—F | | 3.0% |
| 3-HDB(F,F)—F | | 15.0% |
| 3-HHBB(F,F)—F | | 6.0% |
| Composition Example 21 | | |
| F5-B(F)B(F,F)B(F)—OCF₃ | (Compound No.1) | 7.0% |
| F4-B2B(F,F)B(F)—OCF₃ | (Compound No.89) | 7.0% |
| 3-HB—CL | | 10.0% |
| 5-HB—CL | | 5.0% |
| 7-HB—CL | | 5.0% |
| 101-HH-5 | | 6.0% |
| 2-HBB(F)—F | | 8.0% |
| 3-HBB(F)—F | | 8.0% |
| 4-HHB—CL | | 8.0% |
| 5-HHB—CL | | 8.0% |
| 3-H2HB(F)—CL | | 5.0% |
| 3-HBB(F)—F | | 10.0% |
| 5-H2BB(F,F)—F | | 9.0% |
| 3-HB(F)VB-2 | | 4.0% |
| Composition Example 22 | | |
| F5-B(F)2B(F,F)B(F)—CL | (Compound No.79) | 4.0% |
| 2(F)1-BB(F)B(F)—CF₃ | (Compound No.7) | 4.0% |
| 3-HHB(F,F)—F | | 9.0% |
| 3-H2HB(F,F)—F | | 8.0% |
| 4-H2HB(F,F)—F | | 8.0% |
| 3-HBB(F,F)—F | | 21.0% |
| 5-HBB(F,F)—F | | 20.0% |
| 3-H2BB(F,F)—F | | 10.0% |
| 5-HHBB(F,F)—F | | 3.0% |
| 5-HHEBB—F | | 2.0% |
| 3-HH2BB(F,F)—F | | 3.0% |

| | | |
|---|---|---|
| 101-HBBH-4 | | 4.0% |
| 101-HBBH-5 | | 4.0% |
| Composition Example 23 | | |
| F5-B(F)B(F,F)B(F)—OCF₃ | (Compound No.1) | 3.0% |
| F3-B(F,F)B(F)B—CL | (Compound No.9) | 3.0% |
| 2(F)1-BB(F)B(F)—CF₃ | (Compound No.7) | 2.0% |
| 1(FF)3-BB(F)B(F,F)—OCF₃ | (Compound No.13) | 2.0% |
| 5-HB—F | | 12.0% |
| 6-HB—F | | 9.0% |
| 7-HB—F | | 7.0% |
| 2-HHB—OCF₃ | | 7.0% |
| 3-HHB—OCF₃ | | 7.0% |
| 4-HHB—OCF₃ | | 7.0% |
| 5-HHB—OCF₃ | | 5.0% |
| 3-HH2B—OCF₃ | | 4.0% |
| 5-HH2B—OCF₃ | | 4.0% |
| 3-HHB(F,F)—OCF₃ | | 5.0% |
| 3-HBB(F)—F | | 10.0% |
| 3-HH2B(F)—F | | 3.0% |
| 3-HB(F)BH-3 | | 3.0% |
| 5-HBBH-3 | | 3.0% |
| 3-HHB(F,F)—OCF₂H | | 4.0% |
| Composition Example 24 | | |
| F5-B(F)B(F,F)B(F)—OCF₃ | (Compound No.1) | 2.0% |
| FF3-B(F)B(F)B(F)—F | (Compound No.15) | 2.0% |
| 5-H4HB(F,F)—F | | 7.0% |
| 5-H4HB—OCF₃ | | 15.0% |
| 3-H4HB(F,F)—CF₃ | | 8.0% |
| 5-H4HB(F,F)—CF₃ | | 10.0% |
| 3-HB—CL | | 6.0% |
| 2-H2BB(F)—F | | 5.0% |
| 3-H2BB(F)—F | | 10.0% |
| 5-HVHB(F,F)—F | | 5.0% |
| 3-HHB—OCF₃ | | 5.0% |
| 3-H2HB—OCF₃ | | 5.0% |
| V—HHB(F)—F | | 5.0% |
| 3-HHB(F)—F | | 5.0% |
| 5-HHEB—OCF₃ | | 2.0% |
| 3-HBEB(F,F)—F | | 5.0% |
| 5-HH—V2F | | 3.0% |
| Composition Example 25 | | |
| F5-B(F)B(F,F)B(F)—OCF₃ | (Compound No.1) | 3.0% |
| F4-B2B(F,F)B(F)—OCF₃ | (Compound No.89) | 3.0% |
| F2-BB(F)2B(F,F)—CF₃ | (Compound No.115) | 2.0% |
| 2(F)1-BB(F)B(F)—CF₃ | (Compound No.7) | 2.0% |
| 2-HHB(F)—F | | 2.0% |
| 3-HHB(F)—F | | 2.0% |
| 5-HHB(F)—F | | 2.0% |
| 2-HBB(F)—F | | 6.0% |
| 3-HBB(F)—F | | 6.0% |
| 2-H2BB(F)—F | | 9.0% |
| 3-H2BB(F)—F | | 9.0% |
| 3-HBB(F,F)—F | | 25.0% |
| 5-HBB(F,F)—F | | 19.0% |
| 101-HBBH-4 | | 5.0% |
| 101-HBBH-5 | | 5.0% |
| Composition Example 26 | | |
| F3-B(F,F)B(F)B—CL | (Compound No.9) | 7.0% |
| FF3-B(F)B(F)B(F)—F | (Compound No.15) | 6.0% |
| 5-HB—CL | | 12.0% |
| 3-HH-4 | | 7.0% |
| 3-HB-02 | | 15.0% |
| 3-H2HB(F,F)—F | | 8.0% |
| 3-HHB(F,F)—F | | 3.0% |

-continued

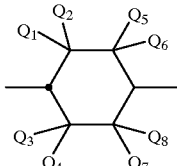

| | |
|---|---|
| 3-HBB(F,F)—F | 6.0% |
| 2-HHB(F)—F | 5.0% |
| 3-HHB(F)—F | 5.0% |
| 5-HHB(F)—F | 5.0% |
| 2-H2HB(F)—F | 2.0% |
| 3-HHBB(F,F)—F | 4.0% |
| 3-HBCF$_2$OB—OCF$_3$ | 4.0% |
| 5-HBCF$_2$OB(F,F)—CF$_3$ | 4.0% |
| 3-HHB-1 | 3.0% |

BEST MODE FOR CARRYING OUT THE INVENTION

The following examples illustrate the present invention more specifically. In each example, C means a crystal, SA means a smectic A phase, SB means a smetic B phase, SX means a smetic phase not determined, N means a nematic phase, Iso means an isotropic phase, and the unit of phase transition temperature is ° C.

EXAMPLE 1

Preparation of 4"-(5-fluoropentyl)-2,3,5-trifluoro-4-iodobiphenyl (Compound represented by general formula (1) wherein m is 0; R is 5-fluoropentyl; X is OCF$_3$; Y$_2$, Y$_6$, Y$_8$ and Y$_{10}$ are F; Y$_1$, Y$_3$, Y$_4$, Y$_5$, Y$_7$, Y$_9$, Y$_{11}$ and Y$_{12}$ are H; and Z$_1$ and Z$_2$ are covalent bonds (Compound No.1))

(Step 1) Preparation of 3-(5-fluoropentyl)fluorobenzene

To a mixture of 4-fluorobutyltriphenylphosphonium bromide 273 g (660 mmol) and tetrahydrofuran (abbreviated THF hereinafter) 1000 ml, potasium-tert-butoxide 88 g (684 mmol) was added under ice cooling and stirred for one hour. Then, under ice cooling, a solution of 3-fluorobenzaldehyde 74 g (596 mmol) in THF 200 ml was added dropwise, and the mixture was stirred for one hour at room temperature. The reaction mixture was poured into hexane 1000 ml, and the crystals deposited were filtered off. The filtrate was concentrated, and distilled (93° C./6 mmHg) to obtain 3-(5-fluoro-1-pentenyl)fluorobenzene 86 g. (Yield:79.6%).

Then, 5% Pd—C 4 g and ethanol 100 ml were added to 3-(5-fluoro-1-pentenyl) fluorobenzene 86 g (472 mmol) to conduct a reaction of catalytic hydrogenation reduction. After the hydrogen absorption was stopped, the catalyst was filtered off, and the filtrate was distilled(62° C./2 mmHg) to obtain 3-(5-fluoropentyl) fluorobenzene 56 g. (Yield: 64.4%).

(Step 2) Preparation of 2-fluoro-4-(5-fluoropentyl) iodobenzene

To a solution of 3-(5-fluoropentyl) fluorobenzene 10.0 g (54.3 mmol), which was obtained at the above step, in THF 50 ml, sec-BuLi (1.05 M, cyclohexane solution) 57 ml (corresponding to 59.7 mmol) was added dropwise so as to maintain −60° C. or less. After the addition, the mixture was stirred for 2 hours. Then, a solution of iodide 15.2 g (59.7 mmol) in THF 60 ml was added dropwise to maintain −60° C. or less, and the mixture was stirred for one hour at the same temperature.

After a solution of 1 N HCl 100 ml was added dropwise to the reaction solution, the mixture was extracted with heptane 150 ml. The resulting organic layer was washed three times with a diluted water solution of NaHCO$_3$ and three times with water, and dried over anhydrous magnesium sulfate. The solvent was distilled off under reduced pressure, and the residue was purified by silica-gel column chromatography (eluent: hexane) to obtain crude 2-fluoro-4-(5-fluoropentyl) iodobenzene 13.7 g. (Yield: 81.8%)

(Step 3) Preparation of 4'-(5-fluoropentyl)-2'1,3,5-trifluorobiphenyl

A mixture of 2-fluoro-4-(5-fluoropentyl) iodobenzene 13.7 g (44.2 mmol) obtained at the above step, dihydroxy (3,5-difluorophenyl) borane 8.3 g (53.0 mmol), K$_2$CO$_3$ 12.2 g (88.3 mmol), 5% Pd—C 1.3 g and mixed solvent of toluene/ethanol/water (1/1/1) 30 ml was heated and refluxed for 8 hours. After the catalyst was filtered off, the mixture was extracted with toluene 200 ml, the resulting organic layer was washed with water three times and dried over anhydrous magnesium sulfate. The solvent was distilled off under reduced pressure, and the residue was purified by silica-gel column chromatography (eluent: heptane) to obtain crude 4'-(5-fluoropentyl)-2',3,5-trifluorobiphenyl 10.5 g.
(Yield: 80.6%).

(Step 4) Preparation of 2'-fluoro-4'-(5-fluoropentyl)-3,5-difluoro-4-iodobiphenyl To a solution of 2'-fluoro-4'-(5-fluoropentyl)-3,5-difluorobiphenyl 5.0 g (16.9 mmol) obtained at the above step in THF 25 ml, n-BuLi (1.6 M, THF solution) 16 ml (corresponding to 25.3 mmol) was added dropwise to maintain at −60° C. or less, and the mixture was stirred at the same temperature for one hour. Then, a solution of iodine 6.6 g (26.2 mmol) in THF 35 ml added dropwise to maintain at −60° C. or less, and the mixture was stirred for one hour at the same temperature.

To the reactant, 1N-HCl 50 ml was added dropwise, and the mixture was extracted with heptane 100 ml. The resulting organic layer was washed three times with a diluted water solution of NaHCO$_3$ and three times with water, and dried over anhydrous magnesium sulfate. The solvent was distilled off under reduced pressure, and the residue was purified by silica-gel column chromatography (eluent: heptane) to obtain crude 2'-fluoro-4'-(5-fluoropentyl)-3,5-difluoro-4-iodobiphenyl 6.1 g. (Yield: 86.2 %)

(Step 5) Preparation of 4"-(5-fluoropentyl)-2,3,5-trifluoro-4-iodobiphenyl

A mixture of 2'-fluoro-4'-(5-fluoropentyl)-3,5-difluoro-4-iodobiphenyl 3.0 g (7.1 mmol) obtained at the above step, dihydroxy(3-fluoro-4-trifluoromethoxy phenyl) borane 1.9 g (9.2 mmol), K$_2$CO$_3$ 2.0 g (14.2 mmol), 5% Pd—C 0.3 g and mixed solvent of toluene/ethanol/water (1/1/1) 30 ml was heated and refluxed for 12 hours. After the catalyst was filtered off, the mixture was extracted with toluene 100 ml, the resulting organic layer was washed with water three times and dried over anhydrous magnesium sulfate. The solvent was distilled off under reduced pressure, and the residue was purified by silica-gel column chromatography (eluent: heptane) to obtain crude 4"-(5-fluoropentyl)-2,3,5-trifluoro-4-iodobiphenyl 3.2 g. The compound was recrystallized from mixed solvent of heptane/ethyl acetate (9/1) to obtain the title compound 1.9 g. (Yield: 56.4%)

The phase transition temperature of the product was C 87.2–88.2 Iso.

The structure was supported well by the spectral data.

Mass spectrum analysis: 474 (M$^+$); $^1$H-NMR (CDCl$_3$, TMS internal standard); δ(ppm); 1.32–2.09 (m, 6H); 2.69 (t, 2H); 4.11–4.82 (d, t, 2H); 6.95–7.34 (m, 8H).

By using the same method as in Example 1, the following compounds can be produced. In the following example, the compounds are represented by abbreviations according to the above rules.
Compound No.2: F2-B(F,F)BB-F
Compound No.3: F3-B(F)B(F)-CF$_3$
Compound No.4: F4-B(F)BB(F)-OCF$_3$
Compound No.5: F5-BB(F,F)B-CF$_2$H
Compound No.6: F6-BB(F)B(F)-OCF$_2$H
Compound No.7: 2(F)1-BB(F)B(F)-CF$_3$
Compound No.8: F7-BBB(F,F)-CF$_3$
Compound No.9: F3-B(F,F)B(F)B-CL
Compound No.10: F9-B(F,F)BB(F)-CL
Compound No.11: F10-B(F)B(F,F)B-CFH$_2$
Compound No.12: F15-BB(F,F)B(F)-OCF$_3$
Compound No.13: 1(FF)3-BB(F)B(F,F)-OCF$_3$
Compound No.14: F20-B(F)B(F)B(F)-CF$_3$
Compound No.15: FF3-B(F)B(F)B(F)-F
Compound No.16: F3-B(F,F)B(F,F)B-OCF$_2$H
Compound No.17: F3-B(F,F)B(F)B(F)-CF$_2$H
Compound No.18: FFF3-B(F,F)B(F)B(F)-OCF$_3$
Compound No.19: F50-B(F)B(F,F)B(F)-CL
Compound No.20: F5-B(F)B(F)B(F,F)-OCF$_3$
Compound No.21: F2-B(F,F)B(F,F)B(F)-CF$_2$H
Compound No.22: F2-B(F,F)B(F)B(F,F)-OCF$_2$H
Compound No.23: F4-B(F)B(F,F)B(F,F)-CL
Compound No.24: F4-B(F,F)B(F,F)B(F,F)-F
Compound No.25: F3-B(F,F)BBB-F
Compound No.26: F3-B(F)B(F)BB-CL
Compound No.27: F3-B(F)BB(F)B-C F$_3$
Compound No.28: F5-B(F)BBB(F)-CF$_2$H
Compound No.29: F5-B(F,F)B(F)BB-CFH$_2$
Compound No.30: F5-B(F,F)BB(F)B-OCF$_3$
Compound No.31: F2-B(F,F)BBB(F)-OCF$_2$H
Compound No.32: F2-B(F)B(F,F)BB-CF$_2$H
Compound No.33: F2-BB(F,F)B(F)B-OCF$_2$H
Compound No.34: F4-BB(F,F)BB(F)-F
Compound No.35: F4-B(F)BB(F,F)B-CL
Compound No.36: F4-BB(F)B(F,F)-OCF$_3$
Compound No.37: F1-BBB(F,F)B(F)-OCF$_3$
Compound No.38: F1-B(F)B(F)B(F)B-CFH$_2$
Compound No.39: F13-B(F,F)B(F,F)BB-CF$_3$
Compound No.40: F7-B(F,F)B(F)B(F)B-CF$_2$H
Compound No.41: F7-B(F,F)B(F)BB(F)-F
Compound No.42: F7-B(F,F)BB(F)B(F)-CL
Compound No.43: F6-B(F,F)BB(F,F)B-OCF$_3$
Compound No.44: F6-B(F,F)BBB(F,F)-CL
Compound No.45: F6-B(F)B(F,F)B(F)B-CF$_2$H
Compound No.46: F9-B(F)B(F,F)BB(F)-CFH$_2$
Compound No.47: F2-BB(F,F)B(F)B(F)-CF$_3$
Compound No.48: F2-BB(F,F)B(F,F)B-OCF$_2$H
Compound No.49: F2B-B(F,F)BB(F,F)-F
Compound No.50: F3-B(F)B(F)B(F,F)B-F
Compound No.51: F3-B(F)BB(F,F)B(F)-OCF$_3$
Compound No.52: F3-BBB(F,F)B(F,F)-CF$_3$
Compound No.53: F3-B(F)B(F)B(F,F)-OCF$_2$H
Compound No.54: F3-B(F)BB(F)B(F,F)-CF$_2$H
Compound No.55: F3-BB(F)B(F)B(F,F)-CFH$_2$
Compound No.56: F4-B(F,F)B(F,F)B(F)B-CL
Compound No.57: F4-B(F,F)B(F,F)BB(F)-F
Compound No.58: F4-B(F,F)B(F)B(F)B(F)-F
Compound No.59: F4-B(F,F)B(F)B(F,F)B-CF$_2$
Compound No.60: F4-B(F,F)BB(F,F)B(F)-OCF$_2$H
Compound No.61: F5-B(F,F)B(F)BB(F,F)-CF$_2$H
Compound No.62: F5-B(F,F)BB(F)B(F,F)-CFH$_2$
Compound No.63: F5-B(F)B(F,F)B(F,F)B-OCF$_3$
Compound No.64: FS-BB(F,F)B(F,F)B(F)-CF$_3$
Compound No.65: F5-B(F)B(F,F)B(F)B(F)-CL
Compound No.66: F6-B(F)B(F,F)BB(F,F)-CF$_3$
Compound No.67: F6-BB(F,F)B(F)B(F,F)-OCF$_3$
Compound No.68: F6-B(F)B(F)B(F,F)B(F)-F
Compound No.69: F6-B(F)BB(F,F)B(F,F)-CL
Compound No.70: F6-BB(F)B(F,F)B(F,F)-OCF$_2$H
Compound No.71: F7-B(F)B(F)B(F)B(F,F)-CF$_2$H
Compound No.72: F7-B(F,F)B(F,F)B(F,F)B-CF$_2$H
Compound No.73: F7-B(F,F)B(F,F)B(F)B(F)-F
Compound No.74: F7-B(F,F)B(F,F)BB(F,F)-CL
Compound No.75: F7-B(F,F)B(F)B(F,F)B(F)-CF$_3$
Compound No.76: F7-B(F,F)BB(F,F)B(F,F)-OCF$_3$
Compound No.77: F705-B(F,F)B(F,F)B(F,F)-OCF$_2$H
Compound No.78: F3-B(F,F)B(F,F)B(F,F)B(F,F)-OCF$_2$CFHCF$_3$

EXAMPLE 2

Preparation of 4'-(2-(2-fluoro-4-(5-fluoropentyl) phenyl) ethyl)-2',6',3-trifluoro-4-chlorobiphenyl (Compound represented by general formula (1) wherein m is 0; R is 5-fluoropentyl; X is Cl; $Y_2$, $Y_6$, $Y_8$ and $Y_{10}$ are F; $Y_1$, $Y_3$, $Y_4$, $Y_5$, $Y_7$, $Y_9$, $Y_{11}$, and $Y_{12}$ are H; $Z_1$ is —(CH$_2$)$_2$— and $Z_2$ is a covalent bond (Compound No.79))

(Step 1) Preparation of 1-(2-hydroxy-2-(2-fluoro-4-(5-fluoro-pentyl)phenyl)ethyl)-3,5-difluorobenzene To a solution of 3-(5-fluoropentyl)fluorobenzene 10.7 g (58.5 mmol) obtained at Step 1 in Example 1 in THF 100 ml, sec-BuLi (1.05 M, cyclohexane solution) 61 ml (corresponding to 64.3 mmol) was added dropwise to maintain at −60° C. or less, and the mixture was stirred at the same temperature for 2 hours. A solution of (3,5-difluorophenyl)acetaldehyde 10.5 g (67.3 mmol) in THF 60 ml was then added dropwise to maintain at −60° C. or less, and the mixture was stirred at the same temperature for 5 hours.

After adding dropwise 1N-HCl 100 ml to the reaction solution, the mixture was extracted with ethyl acetate 150 ml. The resulting organic layer was washed three times with a diluted water solution of NaHCO$_3$ and then three times with water, and dried over anhydrous magnesium sulfate. The solvent was distilled off under reduced pressure, and the residue was purified by silica gel column chromatography (eluent: heptane/ethyl acetate=8/2) to obtain crude 1-(2-hydroxy-2-(2-fluoro-4-(5-fluoropentyl)phenyl)ethyl)-3,5-difluoro benzene 9.9 g. (Yield: 49.5%) (Step 2) Preparation of methyl (1-(2-fluoro-4-(5-fluoropentyl)phenyl)-2-(3,5-difluorophenyl))-O-ethyldithiocarbonate To a mixture of NaOH 30.0 g (749.2 mmol), water 30 ml and tetrabutylammonium hydrogen sulfate 5.1 g (15 mmol), a solution of 1-(2-hydroxy-2-(2-fluoro-4-(5-fluoropentyl) phenyl)ethyl)-3,5-difluoro benzene 5.1 g (15.0 mmol) obtained at the above step in toluene 30 ml was added at room temperature, and the mixture was stirred for one hour. Carbon disulfide 2.7 ml (45 mmol) was added, and the mixture was stirred at room temperature for 30 minutes. Methyl iodide 2.8 ml (45 mmol) was added, and then the mixture was stirred at room temperature for 2 hours. The reaction solution was poured into water 100 ml, and extracted with toluene 100 ml. The resulting organic layer was washed three times with water and dried over anhydrous magnesium sulfate. The solvent was distilled off under reduced pressure, and the residue was purified by silica gel column chromatography (eluent: heptane/toluene=1/1) to obtain crude methyl (1-(2-fluoro-4-(5-fluoropentyl) phenyl)-2-(3,5-difluorophenyl))-O-ethyldithiocarbonate 3.0 g. (Yield: 49.2%)

(Step 3) Preparation of 1-(2-(2-fluoro-4-(5-fluoropentyl) phenyl)ethyl)-3,5-difluorobenzene A mixture of methyl (1-(2-fluoro-4-(5-fluoropentyl) phenyl)-2-(3,5-difluorophenyl))-O-ethyldithiocarbonte 3.0 g (7.3 mmol) obtained at the above step, 2,2'-azobisisobutylonitrile 0.2 g (1.4 mmol) and dried toluene 15 ml was heated at 80° C. , tri-n-butyl tin hydride 3.9 ml (14.5 mmol) was added dropwise, and the mixture was stirred at the same temperature for one hour. The reaction solution was poured into diluted hydrochloric acid 30 ml and extracted with toluene 50 ml. The resulting organic layer was washed three times with a diluted water solution of NaHCO$_3$ and then three times with water, and dried over anhydrous magnesium sulfate. The solvent was distilled off under reduced pressure, and the residue was purified by silica gel column chromatography (eluent: heptane/toluene= 9/1) to obtain crude 1-(2-(2-fluoro-4-(5-fluoropentyl) phenyl)ethyl)-3,5-difluorobenzene 2.1 g. (Yield: 91.1%)

(Step 4) Preparation of 1-(2-(2-fluoro-4-(5-fluoropentyl) phenyl)ethyl)-3,5-difluoro-4-iodobenzene To a solution of 1-(2-(2-fluoro-4-(5-fluoropentyl)phenyl) ethyl)-3,5-difluorobenzene obtained at the above step 2.1 g (6.6 mmol) in THF 20 ml, n-BuLi 6.2 ml (9.9 mmol) was added dropwise to maintain at −60° C. or less, and then the mixture was stirred at the same temperature for 2 hours. A solution of iodine 2.7 g (10.6 mmol) in THF 10 ml was added dropwise to maintain at −60° C. or less, and the mixture was stirred for 2 hours at the same temperature.

After 1 N-HCl 30 ml was added dropwise to the reaction solution, the mixture was extracted with heptane 50 ml. The resulting organic layer was washed three times with a diluted water solution of NaHCO$_3$ and then three times with water, and dried over anhydrous magnesium sulfate. The solvent was distilled off under reduced pressure, and the residue was purified by silica gel column chromatography (eluent: heptane/toluene=1/1) to obtain crude 1-(2-(2-fluoro-4-(5-fluoropentyl)phenyl)ethyl)-3,5-difluoro-4-iodobenzene 2.8 g. (Yield: 98.6 %)

(Step 5) Preparation of 4'-(2-(2-fluoro-4-(5-fluoropentyl) phenyl)ethyl)-2',6',3-trifluoro-4-chlorobiphenyl A mixture of 1-(2-(2-fluoro-4-(5-fluoropentyl)phenyl) ethyl)3,5-difluoro-4-iodobenzene obtained at the above step 2.5 g (5.8 mmol), dihydroxy(3-fluoro-4-chlorophenyl) borane 1.3 g (7.5 mmol), K$_2$CO$_3$ 1.6 g (11.6 nol), 5% Pd—C 0.3 g and mixed solvent of toluene/ethanol/water (1/1/1) 30 ml was refluxed for 13 hours. After the catalyst was filtered off, the mixture was extracted with toluene 100 ml, the resulting organic layer was washed with water three times and dried over anhydrous magnesium sulfate. The solvent was distilled off under reduced pressure, and the resulting residue was purified by silica-gel column chromatography (eluent: heptane/toluene=9/1) to obtain crude 4'-(2-(2-fluoro-4-(5-fluoropentyl) phenyl)ethyl)-2',6',3-trifluoro-4-chlorobiphenyl 1.6 g. The compound was recrystallized from mixed solvent of ethanol/ethyl acetate (85/15) to obtain the title compound 1.3 g. (Yield: 47.7%)

The phase transition temperature of the product was C 53.2–53.6 Iso.

The structure was supported well by the spectral data.

Mass spectrum analysis: 452 (M$^+$); $^1$H-NMR (CDCl$_3$, TMS internal standard); δ(ppm); 1.34–2.03 (m, 6H); 2.61 (t, 2H); 2.92 (s, 4H); 4.11–4.77 (d, t, 2H); 6.95–7.34 (m, 8H).

By using the same method as in Example 2, the following compounds can be produced.
Compound No.80: F3-B(F,F)2BB-F
Compound No.81: F301-B(F)2B(F)B-CL
Compound No.82: F3-B(F)2BB(F)-CF$_3$
Compound No.83: F3-B2B(F,F)B-CF$_2$H
Compound No.84: F3-B2BB(F)B(F)-CFH$_2$
Compound No.85: F3-B2BB(F,F)-OCF$_3$
Compound No.86: F4-B(F,F)2B(F)B-OCF$_2$H
Compound No.87: F4-B(F,F)2BB(F)-F
Compound No.88: F4-B(F)2B(F,F)2B-CL
Compound No.89: F4-B2B(F,F)B(F)-OCF$_3$
Compound No.90: F5-B(F)2B(F)B(F)-OCF$_2$H
Compound No.91: F5-B(F)2BB(F,F)-CL
Compound No.92: F5-B2B(F)B(F,F)-CF$_3$
Compound No.93: F5-B(F,F)2B(F,F)B-OCF$_3$
Compound No.94: F5-B(F=F)2BB(F,F)-OCF$_2$H
Compound No.95: F5-B2B(F,F)B(F,F)-OCF$_2$H
Compound No.96: F2-B(F,F)2B(F)B(F)-CL
Compound No.97: F2-B(F)2B(F,F)B(F)-CFH$_2$
Compound No.98: F2-B(F)2B(F)B(F,F)-F
Compound No.99: F2-B(F,F)2B(F,F)B(F)-CL
Compound No.100: F2-B(F,F)2B(F)B(F,F)-OCF$_3$
Compound No.101: F2-B(F,F)2B(F)B(F,F)-CFH$_2$
Compound No.102: F2-B(F,F)2B(F,F)B(F,F)-OCF$_2$CFHCF$_3$
Compound No.103: F1-B(F,F)B2B-F
Compound No.104: F1-B(F)B(F)2B-CL
Compound No.105: F1-B(F)B2B(F)-CF$_3$
Compound No.106: F1-BB(F,F)2B-CF$_2$H
Compound No.107: F1-BB(F)2B(F)-CFH$_2$
Compound No.108: F1-BB2B(F,F)-OCF$_3$
Compound No.109: F3-B(F,F)B(F)2B-OCF$_2$H
Compound No.110: F3-B(F,F)B2B(F)-F
Compound No.111: F3-B(F)B(F,F)2B-CL
Compound No.112: F3-BB(F,F)2B(F)-OCF$_3$
Compound No.113: F6-B(F)B(F)2B(F)-OCF$_2$H
Compound No.114: F6-B(F)B2B(F,F)-CL
Compound No.115: F2-BB(F)2B(F,F)-CF$_3$
Compound No.116: F6-B(F,F)B(F,F)2B-OCF$_3$
Compound No.117: F6-B(F,F)B2B(F,F)-CF$_2$H
Compound No.118: F6-BB(F,F)2B(F,F)-OCF$_2$H
Compound No.119: F7-B(F,F)B(F)2B(F)-CL
Compound No.120: F7-B(F)B(F,F)2B(F)-CF$_2$H
Compound No.121: F7-B(F)B(F)2B(F,F)-F
Compound No.122: F7-B(F,F)B(F,F)2B(F)-CL
Compound No.123: F7-B(F,F)B(F)2B(F,F)-OCF$_3$
Compound No.124: F7-B(F)B.(FF)2B(F,F)-CF$_2$H
Compound No.125: F7-B(F,F)B(F,F)2B(F,F)-OCF$_2$H
Compound No.126: FF2-B(F)B(F,F)2B(F)-CF$_3$
Compound No.127: 2(F)-B(F)B(F)2B-OCF$_3$
Compound No.128: F1-B(F,F)2BBB-F
Compound No.129: F2-B(F)B(F)2BB-CL
Compound No.130: F3-B(F)BB(F)2B-CF$_3$
Compound No.131: F4-B(F)2BBB(F)-CF$_2$H
Compound No.132: F5-B(F,F)B(F)2BB-CFH$_2$
Compound No.133: F6-B(F,F)BB(F)2B-OCF$_3$
Compound No.134: F7-B(F,F)BB2B(F)-OCF$_2$H
Compound No.135: F8-B(F)2B(F,F)BB-CF$_2$H
Compound No.136: F9-BB(F,F)2BB-OCF$_2$H
Compound No.137: F10-BB(F,F)B2B(F)-F
Compound No.138: F15-B(F)2BB(F,F)B-CL
Compound No.139: F2O-BB(F)2B(F,F)B-OCF$_3$
Compound No.140: F2-BBB(F,F)2B(F)-OCF$_3$
Compound No.141: F3-B(F)2B(F)B(F)B-CF$_2$H
Compound No.142: F4-B(F,F)B(F,F)2BB-CF$_3$
Compound No.143: F5-B(F,F)B(F)B(F)2B-CF$_2$H
Compound No.144: F6-B(F,F)2B(F)BB(F)-F
Compound No.145: F7-B(F,F)B2B(F)B(F)-CL
Compound No.146: F1-B(F,F)BB(F,F)2B-OCF$_3$
Compound No.147: F2-B(F,F)2BBB(F,F)-CL
Compound No.148: F3-B(F)B(F,F)2B(F)B-CF$_2$H
Compound No.149: F4-B(F)B(F,F)B2B(F)-CFH$_2$
Compound No.150: F5-B2B(F,F)B(F)B(F)-CF$_3$
Compound No.151: F6-BB(F,F)2B(F.F)B-OCF$_2$H
Compound No.152: F7-BB(F,F)B2B(F,F)-F Compound No.153: F6-B(F)2B(F)B(F,F)B-OCF$_2$H
Compound No.154: F5-B(F)B2B(FF)B(F)-OCF$_3$
Compound No.155: F4-BBB(F,F)2B(F,F)-CF$_3$
Compound No.156: F3-B(F)2B(F)BB(F,F) -OCF$_2$H
Compound No.157: F2-B(F)B2B(F)B(F,F)-CF$_2$H
Compound No.158: F1-BB(F)B(F)2B(F,F)-CFH$_2$
Compound No.159: F3-B(F,F)2B(F,F)B(F)B-CL
Compound No.160: F3-B(F,F)B(F,F)2BB(F)-F
Compound No.161: F3-B(F,F)B(F)B(F)2B(F)-OCF$_3$
Compound No.162: F3-B(F,F)2B(F)B(F,F)B-CF$_3$
Compound No.163: F3-B(F,F)B2B(F,F)B(F)-OCF$_2$H
Compound No.164: F4-B(F,F)B(F)B2B(F,F)-CF$_2$H
Compound No.165: F4-B(F,F)2BB(F)B(F,F)-CFH$_2$
Compound No.166: F4-B(F)B(F,F)2B(F,F)B-OCF$_3$
Compound No.167: F4-BB(F,F)B(F,F)2B(F)-CF$_3$
Compound No.168: F4-B(F,F)2B(F ,F)B (F)B (F)-CL
Compound No.169: F$_4$-B(F)B(F,F)2B(F,F)—CF$_3$
Compound No.170: F5-BB(F,F)B(F)2B(F,F)-OCF$_3$
Compound No.171: F5-B(F)2B(F)B(F,F)B(F)-F
Compound No.172: F5-B(F)B2B(F,F)B(F,F)-CL
Compound No.173: F5-BB(F)B(F,F)2B(F,F)-OCF$_2$H
Compound No.174: F5-B(F)2B(F)B(F)B(F,F)-CF$_2$H
Compound No.175: F3-B(F,F)B(F,F)B(F)2B(F)-F
Compound No.176: F3-B(F,F)2B(F,F)BB(F,F)-CL
Compound No.177: F30-B(F,F)B(F)2B(F,F)B(F)-CF$_3$
Compound No.178: F3-B(F,F)BB(F,F)2B(F,F)-OCF$_3$
Compound No.179: F3-B(F,F)2B(F)B(F)B(F,F)-OCF$_2$H
Compound No.180: F5-B(F,F)B(F,F)2B(F,F)B(F,F)-CF$_2$H
Compound No.181: F5-B4B(F,F)B(F)-CF$_3$
Compound No.182: F4-B2B(F,F)2B(F,F)-F
Compound No.183: FF2-B(F)B(F,F)2B(F)-CF$_3$
Compound No.184: F-B(F)B(F)4B-CL
Compound No.185: FFF3-B(F)4B(F)B(F,F)B(F)-F
Compound No.186: F3-BB(F)4B(F)B-OCF$_3$
Compound No.187: F3-BB(F)B(F)4B-CF$_3$

EXAMPLE 3

Preparation of (2-fluoro-4-(5-fluoropentyl)phenyl) methyl-2-,3',4'-trifluorobiphenyl-4-yl ether (a compound having general formula (1) in which m is 0; R is 5-fluoropentyl; X is F; Y$_2$, Y$_6$ and Y$_{10}$ are F; Y$_1$, Y$_3$, Y$_4$, Y$_5$, Y$_7$, Y$_8$, Y$_9$, Y$_{11}$ and Y$_{12}$ are H; Z$_1$ is —CH$_2$O— and Z$_2$ is a covalent bond (Compound No.188))

To a mixture of NaH (60%) 0.6 g (160 mmol) and dimethylformamide (abbreviated as DMF hereinafter) 5 ml, 2-fluoro-4-hydroxy-3',4'-difluorobiphenyl (prepared by a coupling reaction of 3-fluoro-4-iodoanisol and dihydroxy(3, 4-difluorophenyl)borane and an elimination reaction of a protective group) 3.0 g (134 mmol) in DMF 30 ml was added dropwise at room temperature, and stirred for one hour. A solution of 2-fluoro-4-(5-fluoropentyl) iodomethylbenzene (prepared by reduction and iodination of 2-fluoro-4-(5-fluoropentyl)benzaldehyde) 6.1 g (187 mmol) in DMF 30 ml was then added dropwise at room temperature, and stirred for 3 hours. The mixture was poured into dilute hydrochloric acid 150 ml, and extracted with toluene 100 ml. The resulting organic layer was washed with a diluted water solution of NaHCO$_3$ and then with water, and dried over anhydrous magnesium sulfate. The solvent was distilled off under reduced pressure, and the residue was purified by silica gel column chromatography (eluent: heptane/toluene=1/1) to obtain crude (2-fluoro-4-(5-fluoropentyl)phenyl) methyl (2-fluoro-4-(5-fluoropentyl) phenyl)methyl-2-3',4'-trifluorobiphenyl-4-yl ether. The compound was recrystallized from mixed solvent of ethanol/ ethyl acetate to obtain the title compound.

According to the same mathod of Example 3, the following compounds can be prepared.
Compound No.189: F5-B(F,F)OCH$_2$B(F)B(F,F)-OCF$_3$
Compound No.190: F4-B(F)C$_3$H$_6$OB(F)B(F)-CL
Compound No.191: F3-B(F)O C$_3$H$_6$BB(F,F)-CF$_3$
Compound No.192: F2-B(F,F)B(F)CH$_2$OB(F)-F
Compound No.193: F3-BB(F)OCH$_2$B(F,F)-OCF$_2$H
Compound No.194: F3-BB(F,F)C$_3$H$_6$OB(F)-OCF$_3$
Compound No.195: F30-B(F)BO C$_3$H$_6$B(F,F)-CF$_3$
Compound No.196: F3-BCH$_2$OB(F)BB(F,F)-CL
Compound No.197: F2-BB(F) CH$_2$OB(F)B(F)-OCF$_3$
Compound No.198: F2-B(F)BBCH$_2$OB(F,F)-OCF$_2$H
Compound No.199: F2-BC$_3$H$_6$OB(F)B(F,F)B-CF$_3$
Compound No.200: F4-BB(F)C$_3$H$_6$OBB(F,F)B(F)-CL
Compound No.201: F5-B(F,F)B(F)BC$_3$H$_6$OB(F,F)-OCF$_3$
Compound No.202: F5-BB(F,F)OC$_3$H$_6$BB(F)-CF$_2$H Examples using the compounds of the present invention as ingredients of the liquid crystal compositions are described as follows. In each using example, NI is nematic phase-isotropic phase transition temperature (° C.), Δε is the value of dielectric anisotropy, Δn is the value of optical anisotropy, η is viscosity (mPa·s), Vth is threshold voltage (V), and VHR is voltage holding ratio (%).

η was measured at 20° C., Δε, Δn, Vth and pitch of twist P(μm) were each measured at 25° C., and the values of VHR in order from the left were measured at 25° C., 80° C. and 100° C., respectively.

EXAMPLE 4

(Using Example 1)

Liquid crystal composition (A) comprising the following cyanophenyl cyclohexane type liquid crystal compounds:

|     |          |     |
| --- | -------- | --- |
|     | 3-HB-C   | 24% |
|     | 5-HB-C   | 36% |
|     | 7-HB-C   | 25% |
| and | 5-HBB-C  | 15% | has the following physical properties.

NI: 71.7, Δε: 11.0, Δn: 0.137, η: 26.7, Vth: 1.78.

The physical values of liquid crystal composition (B) consisting of liquid crystal composition (A) 85% and 4"-(5-fluoropentyl)-2,3,5-trifluoro-4-iodobiphenyl (Compound No. 1) 15%, which was obtained in Example 1, were as follows:

NI: 63.5, Δε: 12.5, Δn: 0.138, η: 34.2, Vth: 1.47.

Although composition (B) was allowed to stand in a freezer at −20° C. for 60 days, the development of the smectic phase and the precipitation of crystals were not found.

EXAMPLE 5

(Using Example 2)

The physical values of liquid crystal composition (C), which was obtained by using the same method as in Example 4, except that 4'-(2-(2-fluoro-4-(5-fluoropentyl) phenyl)ethyl)-2',6',3-trifluoro-4-chlorobiphenyl (Compound No. 79) which was obtained in Example 2 was used instead of 4"-(5-fluoropentyl)-2,3,5-trifluoro-4-iodobiphenyl (Compound No. 1) were as follows: NI: 58.8, Δε: 12.2, Δn: 0.137, η: 35.2, Vth: 1.47.

Although composition (C) was allowed to stand in a freezer at −20° C. for 60 days, the development of the smectic phase and the precipitation of crystals were not found.

EXAMPLE 6

(Using Example 3)

The physical properties of the liquid crystal composition of Composition Example 1 were as follows.

NI: 87.6, Δε: 7.9, Δn: 0.158, η: 22.4, Vth: 1.88, P:11.

Although this composition was allowed to stand in a freezer at −20° C. for 60 days, the development of the smectic phase and the precipitation of crystals were not found.

EXAMPLE 7

(Using Example 4)

The physical properties of the liquid crystal composition of Composition Example 2 were as follows.

NI: 78.4, Δε: 9.3, Δn: 0.153, η: 20.1, Vth: 1.74.

Although this composition was allowed to stand in a freezer at −20° C. for 60 days, the development of the smectic phase and the precipitation of crystals were not found.

EXAMPLE 8

(Using Example 5)

The physical properties of the liquid crystal composition of Composition Example 3 were as follows.

NI: 86.2, Δε: 30.7, Δn: 0.147, η: 89.2, Vth: 0.90.

Although this composition was allowed to stand in a freezer at −20° C. for 60 days, the development of the smectic phase and the precipitation of crystals were not found.

EXAMPLE 9

(Using Example 6)

The physical properties of the liquid crystal composition of Composition Example 4 were as follows.

NI: 93.2, Δε: 7.3, Δn: 0.207, η: 38.3, Vth: 1.89.

Although this composition was allowed to stand in a freezer at −20° C. for 60 days, the development of the smectic phase and the precipitation of crystals were not found.

EXAMPLE 10

(Using Example 7)

The physical properties of the liquid crystal composition of Composition Example 5 were as follows.

NI: 63.2, Δε: 11.9, Δn: 0.120, η: 42.3, Vth: 1.19.

Although this composition was allowed to stand in a freezer at −20° C. for 60 days, the development of the smectic phase and the precipitation of crystals were not found.

EXAMPLE 11

(Using Example 8)

The physical properties of the liquid crystal composition of Composition Example 6 were as follows.

NI: 66.0, Δε: 9.8, Δn: 0.145, η: 28.0, Vth: 1.28.

Although this composition was allowed to stand in a freezer at −20° C. for 60 days, the development of the smectic phase and the precipitation of crystals were not found.

EXAMPLE 12

(Using Example 9)

The physical properties of the liquid crystal composition of Composition Example 7 were as follows.

NI: 73.5, Δε: 23.5, Δn: 0.119, η: 37.5, Vth: 0.99.

Although this composition was allowed to stand in a freezer at −20° C. for 60 days, the development of the smectic phase and the precipitation of crystals were not found.

EXAMPLE 13

(Using Example 10)

The physical properties of the liquid crystal composition of Composition Example 8 were as follows.

NI: 82.5, Δε: 5.7, Δn: 0.117, η: 19.5, Vth: 1.90.

Although this composition was allowed to stand in a freezer at −20° C. for 60 days, the development of the smectic phase and the precipitation of crystals were not found.

EXAMPLE 14

(Using Example 11)

The physical properties of the liquid crystal composition of Composition Example 9 were as follows.

NI: 79.1, Δε: 19.2, Δn: 0.145, η: 45.5, Vth: 0.88.

Although this composition was allowed to stand in a freezer at −20° C. for 60 days, the development of the smectic phase and the precipitation of crystals were not found.

EXAMPLE 15

(Using Example 12)

The physical properties of the liquid crystal composition of Composition Example 10 were as follows.

NI: 56.1, Δε: 11.2, Δn: 0.116, η: 32.9, Vth: 1.03.

Although this composition was allowed to stand in a freezer at −20° C. for 60 days, the development of the smectic phase and the precipitation of crystals were not found.

EXAMPLE 16

(Using Example 13)

The physical properties of the liquid crystal composition of Composition Example 11 were as follows.

NI: 58.7, Δε: 8.5, Δn: 0.157, η: 29.7, Vth: 1.59.

Although this composition was allowed to stand in a freezer at −20° C. for 60 days, the development of the smectic phase and the precipitation of crystals were not found.

EXAMPLE 17

(Using Example 14)

The physical properties of the liquid crystal composition of Composition Example 12 were as follows.

NI: 90.6, Δε: 9.7, Δn: 0.138, η: 23.9, Vth: 1.36.

Although this composition was allowed to stand in a freezer at −20° C. for 60 days, the development of the smectic phase and the precipitation of crystals were not found.

EXAMPLE 18

(Using Example 15)

The physical properties of the liquid crystal composition of Composition Example 13 were as follows.

NI: 88.5, Δε: 8.6, Δn: 0.207, η: 19.2, Vth: 1.72.

Although this composition was allowed to stand in a freezer at −20° C. for 60 days, the development of the smectic phase and the precipitation of crystals were not found.

EXAMPLE 19

(Using Example 16)

The physical properties of the liquid crystal composition of Composition Example 14 were as follows.

NI: 75.4, Δε: 7.3, Δn: 0.128, η: 13.7, Vth: 1.89.

Although this composition was allowed to stand in a freezer at −20° C. for 60 days, the development of the smectic phase and the precipitation of crystals were not found.

EXAMPLE 20

(Using Example 17)

The physical properties of the liquid crystal composition of Composition Example 15 were as follows.

NI: 85.1, Δε: 7.4, Δn: 0.110, η: 26.3, Vth: 1.84.

Although this composition was allowed to stand in a freezer at −20° C. for 60 days, the development of the smectic phase and the precipitation of crystals were not found.

EXAMPLE 21

(Using Example 18)

The physical properties of the liquid crystal composition of Composition Example 16 were as follows.

NI: 89.4, Δε: 7.2Δn: 0.092, η: 29.5, Vth: 1.87, P=79.

Although this composition was allowed to stand in a freezer at −20° C. for 60 days, the development of the smectic phase and the precipitation of crystals were not found.

EXAMPLE 22

(Using Example 19)

The physical properties of the liquid crystal composition of Composition Example 17 were as follows.

NI: 85.9, Δε: 7.1, Δn: 0.111, η: 27.2, Vth: 1.92.

Although this composition was allowed to stand in a freezer at −20° C. for 60 days, the development of the smectic phase and the precipitation of crystals were not found.

EXAMPLE 23

(Using Example 20)

The physical properties of the liquid crystal composition of Composition Example 18 were as follows.

NI: 71.6, Δε: 8.6, Δn: 0.115, η: 28.3, Vth: 1.45.

Although this composition was allowed to stand in a freezer at −20° C. for 60 days, the development of the smectic phase and the precipitation of crystals were not found.

EXAMPLE 24

(Using Example 21)

The physical properties of the liquid crystal composition of Composition Example 19 were as follows.

NI: 69.5, Δε: 10.0, Δn: 0.097, η: 27.2, Vth: 1.10, VHR:97.2, 96.2, 94.9.

Although this composition was allowed to stand in a freezer at −20° C. for 60 days, the development of the smectic phase and the precipitation of crystals were not found.

EXAMPLE 25

(Using Example 22)

The physical properties of the liquid crystal composition of Composition Example 20 were as follows.

NI: 68.2, Δε: 14.2, Δn: 0.093, η: 38.4, Vth: 1.03.

Although this composition was allowed to stand in a freezer at −20° C. for 60 days, the development of the smectic phase and the precipitation of crystals were not found.

EXAMPLE 26

(Using Example 23)

The physical properties of the liquid crystal composition of Composition Example 21 were as follows.

NI: 88.9, Δε: 4.9, Δn: 0.129, η: 21.7, Vth: 2.32.

Although this composition was allowed to stand in a freezer at −20° C. for 60 days, the development of the smectic phase and the precipitation of crystals were not found.

EXAMPLE 27

(Using Example 24)

The physical properties of the liquid crystal composition of Composition Example 22 were as follows.

NI: 93.2, Δε: 9.8, Δn: 0.122, η: 37.1, Vth: 1.54.

Although this composition was allowed to stand in a freezer at −20° C. for 60 days, the development of the smectic phase and the precipitation of crystals were not found.

EXAMPLE 28

(Using Example 25)

The physical properties of the liquid crystal composition of Composition Example 23 were as follows.

NI: 80.0, Δε: 6.2, Δn: 0.095, η: 17.0, Vth: 1.87.

Although this composition was allowed to stand in a freezer at −20° C. for 60 days, the development of the smectic phase and the precipitation of crystals were not found.

EXAMPLE 29

(Using Example 26)

The physical properties of the liquid crystal composition of Composition Example 24 were as follows.

NI: 69.3, Δε: 9.0, Δn: 0.098, η: 27.9, Vth: 1.53.

Although this composition was allowed to stand in a freezer at −20° C. for 60 days, the development of the smectic phase and the precipitation of crystals were not found.

EXAMPLE 30

(Using Example 27)

The physical properties of the liquid crystal composition of Composition Example 25 were as follows.

NI: 88.3, Δε: 8.9, Δn: 0.134, η: 36.7, Vth: 1.57, VHR: 97.1, 96.2, 95.0.

Although this composition was allowed to stand in a freezer at −20° C. for 60 days, the development of the smectic phase and the precipitation of crystals were not found.

EXAMPLE 31

(Using Example 28)

The physical properties of the liquid crystal composition of Composition Example 26 were as follows.

NI: 71.7, Δε: 5.4, Δn: 0.106, η: 22.4, Vth: 1.89.

Although this composition was allowed to stand in a freezer at −20° C. for 60 days, the development of the smectic phase and the precipitation of crystals were not found.

EXAMPLE 32

(Using Example 29)

Liquid crystal composition (D) comprising of the following liquid crystal compounds of a fluorine type:

| | |
|---|---|
| 7-HB(F,F)-F | 6% |
| 3-H2HB(F,F)-F | 10% |
| 5-H2HB(F,F)-F | 10% |
| 3-HHB(F,F)-F | 11% |
| 4-HHB(F,F)-F | 6% |
| 3-HH2B(F,F)-F | 15% |
| 5-HH2B(F,F)-F | 12% |
| 3-HBB(F,F)-F | 6% |
| 5-HBB(F,F)-F | 6% |

| | |
|---|---|
| 3-HHEB(F,F)-F | 10% |
| 4-HHEB(F,F)-F | 4% |
| 5-HHEB(F,F)-F | 4% | was allowed to stand in a freezer at −20° C., and as a result, the precipitation of crystals were found at the 9$^{th}$ day.

Liquid crystal composition (E) was obtained by replacing 3HH2B(F,F)-F in this liquid crystal composition (D) with 4'-(2-(2-fluoro-4-(5-fluoropentyl) phenyl)ethyl)-2',6',3-trifluoro-4-chlorobiphenyl (Compound No. 79) obtained in Example 4. Although this composition was allowed to stand in a freezer at −20° C. for 34 days, the development of the smectic phase and the precipitation of crystals were not found.

As described above, by using the compounds of the present invention, it is found that the compatibility is improved at low temperature.

INDUSTRIAL APPLICABILITY

The liquid crystalline compounds of the present invention have a very high voltage holding ratio, very little variation of this property depending on temperature and high Δn, and these compounds can be easily mixed with several kinds of liquid crystal materials and have good compatibility under a low temperature. Moreover, novel liquid crystalline compounds having desired physical properties can be provided by suitably selecting the substituent groups and bonding groups of the liquid crystalline compounds of the present invention.

Accordingly, by using the liquid crystalline compounds of the present invention as constituents of liquid crystal compositions, novel liquid crystal compositions having very high voltage holding ratio, very little variation of this property depending on temperature, suitable Δn and Δε values and excellent stability, and liquid crystal display devices constituted by using the liquid crystal compositions can be provided.

What is claimed is:

1. A liquid crystalline compound represented by formula (1):

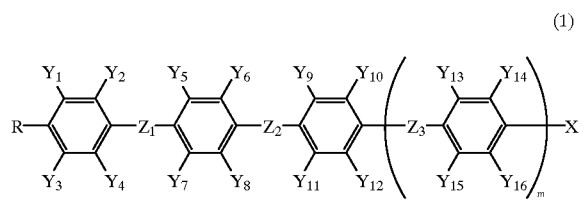

(1)

wherein R represents an alkyl, alkoxy or alkoxyalkyl group of 2–20 carbon atoms, and in each group, and one hydrogen atom is replaced by a fluorine atom; X is a halogen atom or —CF$_3$—, —CF$_2$H, —CFH$_2$, —OCF$_3$, and —OCF$_2$H; Z$_1$, Z$_2$ and Z$_3$, each independently, represents —(CH$_2$)$_2$—, —(CH$_2$)$_4$—, —CH$_2$O—, —OCH$_2$—, —(CH$_2$)$_3$O—, —O(CH$_2$, $_3$— or covalent bond; Y$_1$, Y$_3$, Y$_5$, Y$_7$, Y$_9$, Y$_{11}$, Y$_{13}$ and Y$_{15}$ are hydrogen atoms, and Y$_2$, Y$_4$, Y$_6$, Y$_8$, Y$_{10}$, Y$_{12}$, Y$_{14}$ and Y$_{16}$ each independently represent hydrogen atoms or fluorine atoms, but at least two of Y$_2$, Y$_4$, Y$_6$, Y$_8$, Y$_{10}$, Y$_{12}$, Y$_{14}$ and Y$_{16}$ are fluorine atoms; m represents 0 or 1, and any atom constituting the compound may be replaced by an isotope thereof.

2. The liquid crystalline compound according to claim 1, wherein m is 0.

3. The liquid crystalline compound according to claim 1, wherein m is 1.

4. The liquid crystalline compound according to claim 2, wherein one hydrogen atom in R is substituted by a fluorine atom.

5. The liquid crystalline compound according to claim 3, wherein one hydrogen atom in R is substituted by a fluorine atom.

6. A liquid crystal composition, comprising at least one of liquid crystalline compounds described in claim 1.

7. A liquid crystal composition, comprising as the first component thereof at least one of the compounds described in claim 1, and as the second component thereof at least one compound selected from the group consisting of the compounds represented by formula (2), (3) or (4):

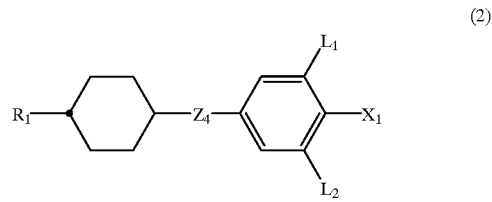

(2)

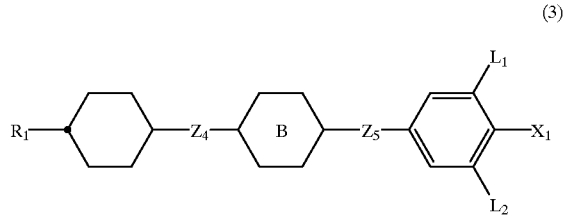

(3)

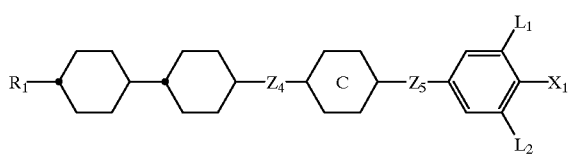

(4)

wherein R$_1$ represents an alkyl group of 1–10 carbon atoms, any nonadjacent methylene groups in the alkyl group may be substituted by oxygen atoms or —CH═CH—, and any hydrogen atoms in the alkyl group may be substituted by fluorine atoms; X$_1$ represents a fluorine atom, a chlorine atom, —OCF$_3$, —OCF$_2$H, —CF$_3$, —CF$_2$H, —CFH$_2$, —OCF$_2$CF$_2$H or —OCF$_2$CFHCF$_3$; L$_1$ and L$_2$ independently represent a hydrogen atom or a fluorine atom; Z$_4$ and Z$_5$ independently represent a 1,2-ethylene group, 1,4-butylene group, —COO—, —CF$_2$O—, —OCF$_2$—, —CH═CH— or a covalent bond, ring B represents trans-1,4-cyclohexylene, 1,3-dioxane-2,5-diyl or 1,4-phenylene whose hydrogen atoms may be substituted by fluorine atoms; ring C represents trans-1,4-cyclohexylene, or 1,4-phenylene whose hydrogen atoms may be substituted by fluorine atoms; and any atom constituting these compounds may be substituted by its isotope.

8. A liquid crystal composition, characterized in that it comprises as a first component thereof at least one of the compounds described in claim 1, and as a second component thereof at least one compound selected from the group consisting of the compounds represented by formula (5) or (6):

(5)

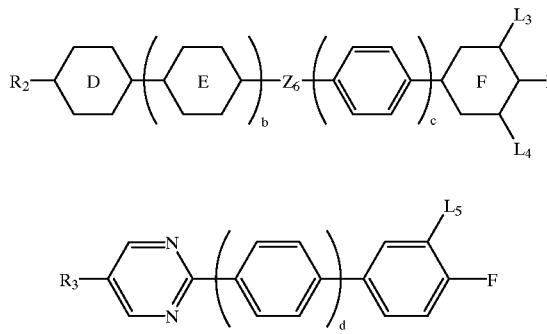

(6)

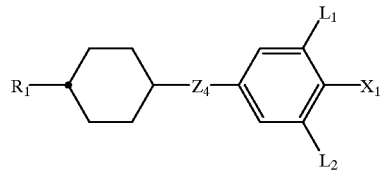

$R_2$ and $R_3$ independently represent an alkyl group of 1–10 carbon atoms, any nonadjacent methylene groups in the alkyl group may be substituted by oxygen atoms or —CH=CH—, and any hydrogen atoms in the alkyl group may be substituted by fluorine atoms, $X_2$ represents —CN group or —C≡C—CN—; ring D represents trans-1,4-cyclohexylene, 1,4-phenylene, 1,3-dioxane-2,5-diyl or pyrimidine-2,5-diyl; ring E represents trans-1,4-cyclohexylene, 1,4-phenylene whose hydrogen atoms may be substituted by fluorine atoms, or pyrimidine-2,5-diyl; ring F represents trans-1,4-cyclohexylene or 1,4-phenylene; $Z_6$ represents a 1,2-ethylene group, —COO— or a covalent bond; $L_3$, $L_4$ and $L_5$ independently represent a hydrogen atom or a fluorine atom; b, c and d independently represent 0 or 1; and any atom constituting these compounds may be substituted by its isotope.

9. A liquid crystal composition, comprising the liquid crystal composition described in claim 6 and at least one optically active compound.

10. A liquid crystal display device comprising the liquid crystal composition described in claim 6.

11. A liquid crystal composition comprising as a first component thereof at least one compound according to claim 1, as a second component thereof at least one compound selected from the group consisting of the compounds of formula (2), (3), or (4)

(2)

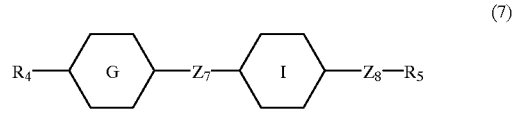

(3)

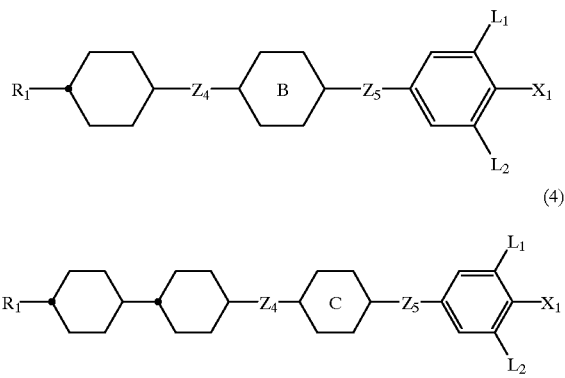

(4)

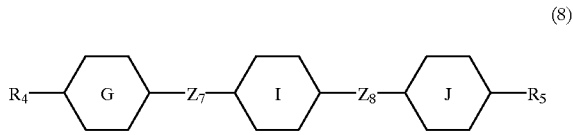

wherein $R_1$ represents an alkyl group of 1–10 carbon atoms, any nonadjacent methylene groups in the alkyl group may be substituted by oxygen atoms or —CH=CH—, and any hydrogen atoms in the alkyl group may be substituted by fluorine atoms; $X_1$ represents a fluorine atom, a chlorine atom, —OCF$_3$, —OCF$_2$H, —CF$_3$, —CF$_2$H, —CFH$_2$, —OCF$_2$CF$_2$H or —OCF$_2$CFHCF$_3$; $L_1$ and $L_2$ independently represent a hydrogen atom or a fluorine atom; $Z_4$ and $Z_5$ independently represent a 1,2-ethylene group, 1,4-butylene group, —COO—, —CF$_2$O—, —OCF$_2$—, —CH=CH— or a covalent bond, ring B represents trans-1,4-cyclohexylene, 1,3-dioxane2,5-diyl or 1,4-phenylene whose hydrogen atoms may be substituted by fluorine atoms; ring C represents trans-1,4-cyclohexylene, or 1,4-phenylene whose hydrogen atoms may be substituted by fluorine atoms; and any atom constituting these compounds may be substituted by its isotope;

and as a third component thereof at least one compound selected from the group consisting of the compounds of formula (7), (8), or (9):

(7)

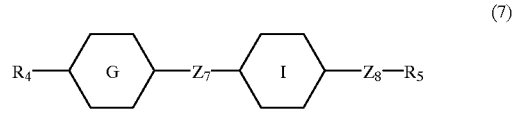

(8)

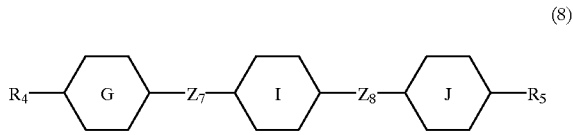

(9)

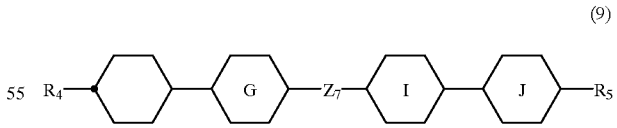

wherein $R_4$ and $R_5$ independently represent an alkyl group of 1–10 carbon atoms, any nonadjacent methylene groups in the alkyl group may be substituted by oxygen atoms or —CH=CH—, and any hydrogen atoms in the alkyl group may be substituted by fluorine atoms; ring G, ring I and ring J independently represent trans-1,4-cyclohexylene, pyrimidine-2,5-diyl, or 1,4-phenylene whose hydrogen atoms may be substituted by fluorine atoms; $Z_7$ and $Z_8$ independently represent —C≡C—, —COO—, —CH$_2$CH$_2$—, —CH=CH— or a covalent bond; and any atom constituting these compounds may be substituted by its isotope.

12. A liquid crystal composition comprising as a first component thereof at least one compound according to claim 1, as a second component thereof at least one compound selected from the group consisting of the compounds of formula (5) or

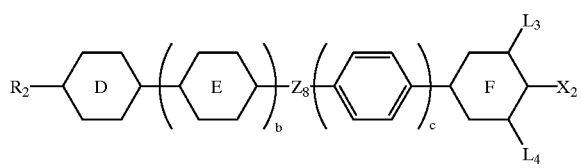

(5)

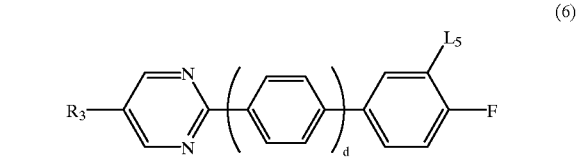

(6)

wherein $R_2$ and $R_3$ independently represent an alkyl group of 1–10 carbon atoms, any nonadjacent methylene groups in the alkyl group may be substituted by oxygen atoms or —CH=CH—, and any hydrogen atoms in the alkyl group may be substituted by fluorine atoms, $X_2$ represents —CN group or —C≡C—CN—; ring D represents trans-1,4-cyclohexylene, 1,4,-phenylene, 1,3-dioxane-2,5-diyl or pyrimidine-2,5-diyl; ring E represents trans-1,4-cyclohexylene, 1,4-phenylene whose hydrogen atoms may be substituted by fluorine atoms, or pyrimidine-2,5-diyl; ring F represents trans-1,4-cyclohexylene or 1,4-phenylene; $Z_6$ represents a 1,2-ethylene group, —COO— or a covalent bond; $L_3$, $L_4$ and $L_5$ independently represent a hydrogen atom or a fluorine atom; b, c and d independently represent 0 or 1; and any atom constituting these compounds may be substituted by its isotope;

and as a third component the reof at least one compound selected from the group consisting of the compounds of formula (7), (8), or (9):

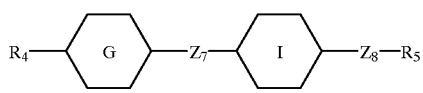

(7)

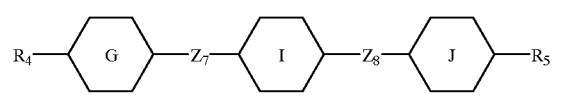

(8)

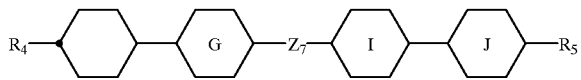

(9)

wherein $R_4$ and $R_5$ independently represent an alkyl group of carbon atoms of 1–10, any nonadjacent methylene groups in the alkyl group may be substituted by oxygen atoms or —CH=CH—, and any hydrogen atoms in the alkyl group may be substituted by fluorine atoms; ring G, ring I and ring J independently represent trans-1,4-cyclohexylene, pyrimidine-2,5-diyl, or 1,4-phenylene whose hydrogen atoms may be substituted by fluorine atoms; $Z_7$ and $Z_8$ independently represent —C≡C—, —COO—, —CH$_2$CH$_2$—, —CH=CH— or a covalent bond; and any atom constituting these compounds may be substituted by its isotope.

13. A liquid crystal composition comprising as a first component thereof at least one compound according to claim 1, as a second component thereof at least one compound selected from the group consisting of the compounds of formula (2), (3), or (4)

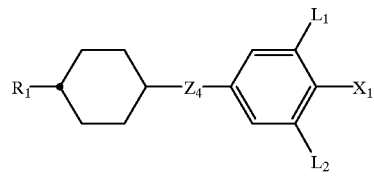

(2)

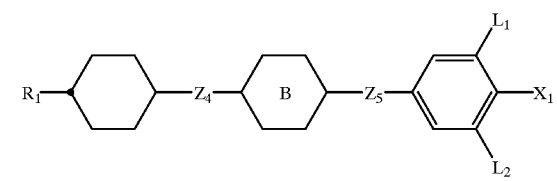

(3)

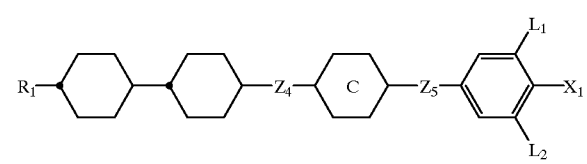

(4)

wherein $R_1$ represents an alkyl group of 1–10 carbon atoms, any nonadjacent methylene groups in the alkyl group may be substituted by oxygen atoms or —CH=CH—, and any hydrogen atoms in the alkyl group may be substituted by fluorine atoms; $X_1$ represents a fluorine atom, a chlorine atom, —OCF$_3$, —OCF$_2$H, —CF$_3$, —CF$_2$H, —CFH$_2$, —OCF$_2$CF$_2$H or —OCF$_2$CFHCF$_3$; $L_1$ and $L_2$ independently represent a hydrogen atom or a fluorine atom; $Z_4$ and $Z_5$ independently represent a 1,2-ethylene group, 1,4-butylene group, —COO—, —CF$_2$O—, —OCF$_2$—, —CH=CH— or a covalent bond, ring B represents trans-1,4-cyclohexylene, 1,3-dioxane2,5-diyl or 1,4-phenylene whose hydrogen atoms may be substituted by fluorine atoms; ring C represents trans-1,4-cyclohexylene, or 1,4-phenylene whose hydrogen atoms may be substituted by fluorine atoms; and any atom constituting these compounds may be substituted by its isotope;

as a third component thereof at least one compound selected from the group consisting of the compounds represented by formula (5) or (6)

(5)

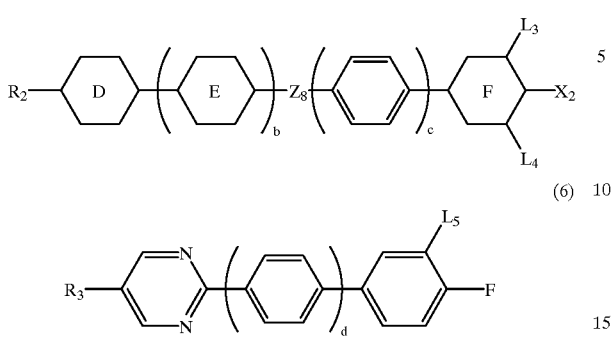

(6)

(7)

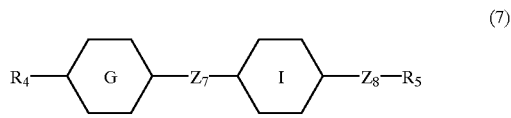

(8)

(9)

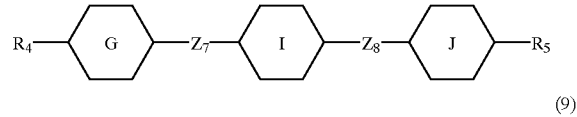

wherein $R_2$ and $R_3$ independently represent an alkyl group of 1–10 carbon atoms, any nonadjacent methylene groups in the alkyl group may be substituted by oxygen atoms or —CH=CH—, and any hydrogen atoms in the alkyl group may be substituted by fluorine atoms, $X_2$ represents —CN group or —C≡C—CN—; ring D represents trans-1,4-cyclohexylene, 1,4,-phenylene, 1,3-dioxane-2,5-diyl or pyrimidine-2,5-diyl; ring E represents trans-1,4-cyclohexylene, 1,4-phenylene whose hydrogen atoms may be substituted by fluorine atoms, or pyrimidine-2,5-diyl; ring F represents trans-1,4-cyclohexylene or 1,4-phenylene; $Z_6$ represents a 1,2-ethylene group, —COO— or a covalent bond; $L_3$, $L_4$ and $L_5$ independently represent a hydrogen atom or a fluorine atom; b, c and d independently represent 0 or 1; and any atom constituting these compounds may be substituted by its isotope and as a fourth component thereof at least one compound selected from the group consisting of the compounds of formula (7), (8), or (9):

wherein $R_4$ and $R_5$ independently represent an alkyl group of carbon atoms of 1–10, any nonadjacent methylene groups in the alkyl group may be substituted by oxygen atoms or —CH=CH—, and any hydrogen atoms in the alkyl group may be substituted by fluorine atoms; ring G, ring I and ring J independently represent trans-1,4-cyclohexylene, pyrimidine-2,5-diyl, or 1,4-phenylene whose hydrogen atoms may be substituted by fluorine atoms; $Z_7$ and $Z_8$ independently represent —C≡C—, —COO—, —CH$_2$CH$_2$—, —CH=CH— or a covalent bond; and any atom constituting these compounds may be substituted by its isotope.

* * * * *